US012139735B2

(12) United States Patent
Prentice

(10) Patent No.: US 12,139,735 B2
(45) Date of Patent: *Nov. 12, 2024

(54) CELL CULTURE PROCESS

(71) Applicant: Momenta Pharmaceuticals, Inc., Cambridge, MA (US)

(72) Inventor: Holly Prentice, Carlisle, MA (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 809 days.

This patent is subject to a terminal disclaimer.

(21) Appl. No.: 17/032,806

(22) Filed: Sep. 25, 2020

(65) Prior Publication Data

US 2021/0246477 A1   Aug. 12, 2021

Related U.S. Application Data

(63) Continuation of application No. 16/780,444, filed on Feb. 3, 2020, now abandoned, which is a continuation of application No. 15/882,857, filed on Jan. 29, 2018, now Pat. No. 10,584,365, which is a continuation of application No. 15/261,270, filed on Sep. 9, 2016, now Pat. No. 9,914,951, which is a continuation of application No. 14/131,005, filed as application No. PCT/US2012/045848 on Jul. 6, 2012, now Pat. No. 9,475,858.

(60) Provisional application No. 61/505,681, filed on Jul. 8, 2011.

(51) Int. Cl.
*C07K 16/00* (2006.01)
*C12P 21/00* (2006.01)
*C12P 21/02* (2006.01)

(52) U.S. Cl.
CPC ............ *C12P 21/005* (2013.01); *C07K 16/00* (2013.01); *C12P 21/02* (2013.01); *C07K 2317/14* (2013.01)

(58) Field of Classification Search
None
See application file for complete search history.

(56) References Cited

U.S. PATENT DOCUMENTS

| 5,087,695 | A | 2/1992 | McAuley |
| 6,900,056 | B2 | 5/2005 | Lee et al. |
| 8,232,075 | B2 | 7/2012 | Luan et al. |
| 8,852,889 | B2 | 10/2014 | Prentice |
| 8,956,830 | B2 | 2/2015 | Prentice et al. |
| 9,475,858 | B2 | 10/2016 | Prentice |
| 9,677,105 | B2 | 6/2017 | Collins et al. |
| 9,914,951 | B2 | 3/2018 | Prentice |
| 10,584,365 | B2 | 3/2020 | Prentice |
| 2004/0106547 | A1 | 6/2004 | Larsen et al. |
| 2010/0297697 | A1 | 11/2010 | Ambrosius et al. |
| 2013/0344084 | A1 | 12/2013 | Subramanian et al. |
| 2014/0142286 | A1 | 5/2014 | Prentice |
| 2016/0376624 | A1 | 12/2016 | Prentice |
| 2018/0187230 | A1 | 7/2018 | Prentice |

FOREIGN PATENT DOCUMENTS

| WO | WO-01/44442 A1 | 6/2001 |
| WO | WO-2008/063892 A2 | 5/2008 |
| WO | WO-2010/071800 A1 | 6/2010 |

OTHER PUBLICATIONS

Beck et al., Characterization by liquid chromatography combined with mass spectrometry of monoclonal anti-IGF-1 receptor antibodies produced in CHO and NS0 cells, Journal of Chromatography B, 819:203-218 (2005).
Dick et al., C-Terminal Lysine Variants in Fully Human Monoclonal Antibodies: Investigation of Test Methods and Possible Causes, Biotechnology and Bioengineering, 100(6):1132-1143 (2008).
Dionex, Monitoring Monoclonal Antibody Heterogeneity by Cation-Exchange Chromatography, Application Note 127 (2009).
Dionex, Product Manual for ProPac WCX-10 and ProPac SCX-10 (pp. 1-30) (2007).
Dionex, ProPac Ion Exchange Columns for Protein Analysis (2006).
Extended European Search Report for EP12810966, 2 pages (May 12, 2015).
Fricker et al., Isolation and Sequence Analysis of cDNA for Rat Carboxypeptidase E [EC 3.4.17.10], A Neuropeptide Processing Enzyme, J. Mol. Endocrinol., 3:666-673 (1989).
Harris et al., Processing of C-terminal lysine and arginine residues of proteins isolated from mammalian cell culture, J. Chromatog. A, 705(1):129-134 (1995).
Hintersteiner, B. et al., Charge heterogeneity: Basic antibody charge variants with increased binding to Fc receptors, MAbs, (8):1548-1560 (2016).
Hook, V.Y.H., Arginine and Lysine Product Inhibition of Bovine Andrenomedullary Carboxypeptidase H, A Prohormone Processing Enzyme, Life Sciences, 47(13):1135-1139 (1990).
International Preliminary Report on Patentability for PCT/US2012/045848, mailed Jan. 23, 2014, published as WO 2013/09648 (7 pages).
International Search Report for PCT/US2012/045848, mailed Dec. 21, 2012, published as WO 2013/09648 (6 pages).
Li, S-X et al., Advances in Carboxypeptidase B, Pharmaceutical Biotechnology, English Abstract, 302-305 (2006).
Luo, J. et al., Probing of C-terminal lysine variation in a recombinant monoclonal antibody production using Chinese hamster ovary cells with chemically defined media, Biotechnol Bioeng, 109(9):2306-15 (2012).
Manser et al., Human Carboxypeptidase E, Biochem. J., 267:517-525 (1990).
No Author Listed, Scientific Discussion of Humira, EMEA, 25 pages (2004).
Reznick et al., Carboxypeptidases from A to Z: implications in embryonic development and Wnt binding, Cell. Mol. Life Sci., 58:1790-1804 (2001).

(Continued)

*Primary Examiner* — Michail A Belyavskyi
(74) *Attorney, Agent, or Firm* — Choate, Hall & Stewart LLP; Rolando Medina; Meaghan E. Bychowski

(57) ABSTRACT

Polypeptides having target levels of C-terminal variants are described.

20 Claims, 1 Drawing Sheet

(56) References Cited

OTHER PUBLICATIONS

Sun et al., Interaction of angiotensin-converting enzyme (ACE) with membrane-bound carboxypeptidase M (CPM)—a new function of ACE, Biol. Chem., 389:1477-1485 (2008).
Tan et al., Molecular Cloning and Sequencing of the cDNA for Human Membrane-bound Carboxypeptidase M, J. Biol. Chem., 264:13165-13170 (1989).
Tan et al., The Deduced Protein Sequence of the Human Carboxypeptidase N High Molecular Weight Subunit Reveals the Presence of Leucine-rich Tandem Repeats, J. Biol. Chem., 265:13-19 (1990).
Valliere-Douglass et al., Separation of populations of antibody variants by fine tuning of hydrophobic-interaction chromatography operating conditions, Journal of Chromatography A., 1214:81-89 (2008).
Vlasak et al., Heterogeneity of Monoclonal Antibodies Revealed by Charge-Sensitive Methods, Current Pharmaceutical Biotechnology, 9:468-481 (2008).
Wolff et al., The Kinetics of Carboxypeptidase B Activity, J. Biol. Chem., 237(10):3094-3099 (1962).
Written Opinion for PCT/US2012/045848, mailed Dec. 21, 2012, published as WO 2013/09648 (10 pages).

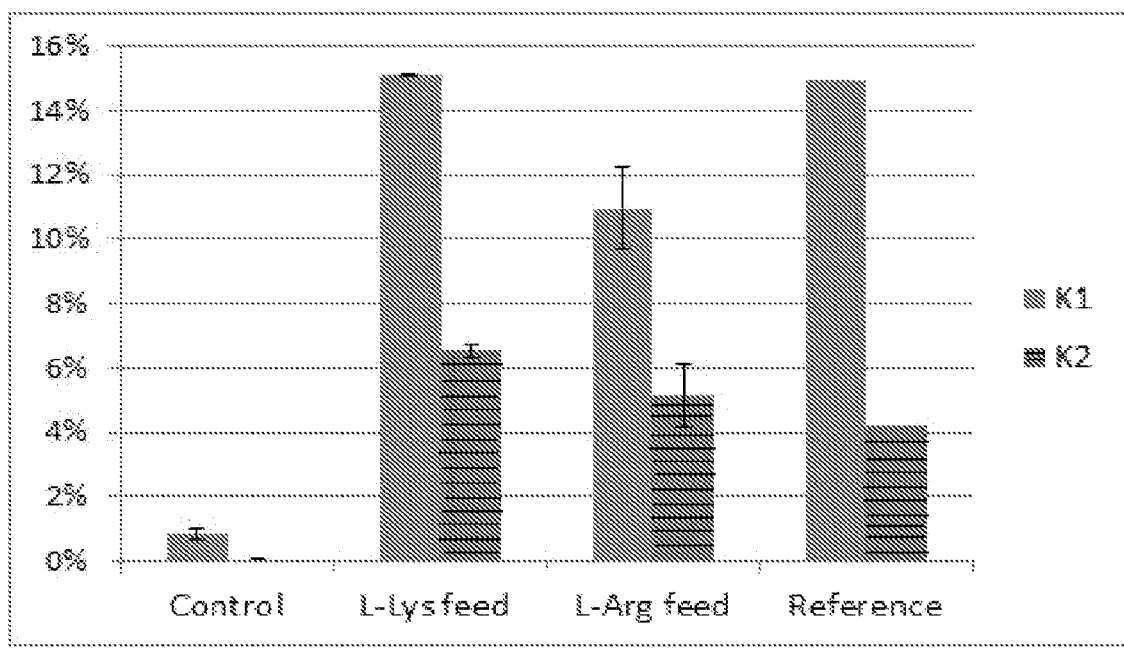

CELL CULTURE PROCESS

CROSS REFERENCE TO RELATED APPLICATIONS

The present application is a continuation of U.S. application Ser. No. 16/780,444, filed Feb. 3, 2020, which is a continuation of U.S. application Ser. No. 15/882,857, filed Jan. 29, 2018, now issued as U.S. Pat. No. 10,584,365, which is a continuation of U.S. application Ser. No. 15/261,270, filed Sep. 9, 2016, now issued at U.S. Pat. No. 9,914,951, which is a continuation of U.S. application Ser. No. 14/131,005, filed Jan. 6, 2014, now issued as U.S. Pat. No. 9,475,858, which is the National Stage of International Application No. PCT/US2012/045848, filed Jul. 6, 2012, which claims the benefit of U.S. provisional application Ser. No. 61/505,681, filed on Jul. 8, 2011, the contents of all of which are herein incorporated by reference in their entirety.

FIELD OF THE INVENTION

The invention relates generally to cell culture methods.

BACKGROUND

Therapeutic polypeptides are an important class of therapeutic biotechnology products, and therapeutic antibodies (including murine, chimeric, humanized and human antibodies and fragments thereof) account for the majority of therapeutic biologic products.

SUMMARY

In one aspect, the invention features a method of producing a population of recombinant polypeptides, comprising: providing a target value of C-terminal variants of a recombinant polypeptide, providing a host cell comprising a nucleic acid encoding the recombinant polypeptide, culturing the host cell under conditions (i) in which the cell expresses a population of C-terminal variants of the encoded recombinant polypeptide and (ii) which increase the intracellular pH of the cell, and isolating the population, wherein the population comprises the provided target value of C-terminal variants of the recombinant polypeptide.

In some embodiments, the conditions which increase the intracellular pH of the cell comprise culturing the cells in a medium comprising one or more of: (a) about 1 g/L to about 50 g/L lysine, arginine and/or histidine; (b) about 0.1 g/L glucose to about 10 g/L glucose; (c) about 2 mM to about 10 mM $NH_4Cl$; (d) about 10 µM to about 500 µM chloroquine; and (e) about 10 mM to about 30 mM glutamine.

In some embodiments, intracellular pH is increased by at least about 10%, at least about 20%, at least about 30%, at least about 40%, at least about 50%, at least about 60%, at least about 70%, at least about 80%, at least about 90%, at least about 100%, or more, relative to control culture conditions. In some embodiments, intracellular pH is increased by a value of at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, or more, relative to control culture conditions.

In some embodiments, the target value is a level of polypeptides comprising a lysine or an arginine residue at a carboxyl terminus. In some embodiments, the target value is a level of polypeptides comprising a lysine or an arginine residue at a carboxyl terminus relative to a sum of a level of polypeptides comprising a lysine or an arginine residue at a carboxyl terminus and a level of polypeptides not comprising a lysine or an arginine residue at a carboxyl terminus. In some embodiments, the level of polypeptides comprising a lysine or an arginine residue at a carboxyl terminus relative to the sum of the level of polypeptides comprising a lysine or an arginine residue at a carboxyl terminus and the level of polypeptides not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the recombinant polypeptide is a recombinant Fc-containing polypeptide (e.g., antibody). In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises measuring a level of one or more C-terminal variants in the population. In some embodiments, the population is a population of Fc-containing polypeptides or antibodies, and the method further comprises measuring a level of one or more of K0, K1, or K2 lysine variants in the population. In some embodiments, the method further comprises recording the level of one or more of K0, K1, or K2 lysine variants in a print or computer-readable medium, e.g., in a test report, Material Safety Data Sheet (MSDS) or Certificate of Testing or Certificate of Analysis (CofA).

In another aspect, the invention features a method of producing a population of Fc-containing polypeptides, comprising: providing a target value of K0, K1, and/or K2 lysine variants of an Fc-containing polypeptide; providing a host cell comprising a nucleic acid encoding the Fc-containing polypeptide; culturing the host cell under conditions (i) in which the cell expresses a population of K0, K1, and/or K2 lysine variants of the encoded Fc-containing polypeptide and (ii) which increase the intracellular pH of the cell; and isolating the population, wherein the population comprises the provided target value of K0, K1, and/or K2 lysine variants of the Fc-containing polypeptide.

In some embodiments, the conditions which increase the intracellular pH of the cell comprise culturing the cells in a medium comprising one or more of: (a) about 2 g/L to about 50 g/L lysine, arginine and/or histidine; (b) about 0.1 g/L glucose to about 10 g/L glucose; (c) about 2 mM to about 10 mM NH$_4$Cl; (d) about 10 µM to about 500 µM chloroquine; and (e) about 10 mM to about 30 mM glutamine.

In some embodiments, the conditions which increase the intracellular pH of the cell comprise culturing the cells in a medium comprising one or more of: (a) at least about 1 g/L lysine, arginine or histidine; (b) about 0.5 g/L glucose to about 2 g/L glucose; (c) about 2 mM to about 10 mM NH$_4$Cl; (d) about 10 µM to about 500 µM chloroquine; and (e) about 10 mM to about 30 mM glutamine.

In some embodiments, intracellular pH is increased by at least about 10%, at least about 20%, at least about 30%, at least about 40%, at least about 50%, at least about 60%, at least about 70%, at least about 80%, at least about 90%, at least about 100%, or more, relative to control culture conditions. In some embodiments, intracellular pH is increased by a value of at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, or more, relative to control culture conditions.

In some embodiments, the target value is a level of Fc-containing polypeptides comprising a lysine or an arginine residue at a carboxyl terminus. In some embodiments, the target value is a level of Fc-containing polypeptides comprising a lysine or an arginine residue at a carboxyl terminus relative to a sum of a level of Fc-containing polypeptides comprising a lysine or an arginine residue at a carboxyl terminus and a level of Fc-containing polypeptides not comprising a lysine or an arginine residue at a carboxyl terminus. In some embodiments, the level of Fc-containing polypeptides comprising a lysine or an arginine residue at a carboxyl terminus relative to the sum of the level of Fc-containing polypeptides comprising a lysine or an arginine residue at a carboxyl terminus and the level of Fc-containing polypeptides not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises measuring a level of one or more of K0, K1, or K2 lysine variants in the population. In some embodiments, the method further comprises recording the level of one or more of K0, K1, or K2 lysine variants in a print or computer-readable medium. e.g., in a test report, Material Safety Data Sheet (MSDS) or Certificate of Testing or Certificate of Analysis (CofA).

In another aspect, the invention features a method of producing a population of antibodies, comprising: providing a target value of K0, K1, and/or K2 lysine variants of an antibody; providing a host cell comprising a nucleic acid encoding the antibody; culturing the host cell under conditions (i) in which the cell expresses a population of K0, K1, and/or K2 lysine variants of the encoded antibody and (ii) which increase the intracellular pH of the cell; and isolating the population, wherein the population comprises the provided target value of K0, K1, and/or K2 lysine variants of the antibody.

In some embodiments, the conditions which increase the intracellular pH of the cell comprise culturing the cells in a medium comprising one or more of: (a) about 2 g/L to about 50 g/L lysine, arginine and/or histidine; (b) about 0.1 g/L glucose to about 10 g/L glucose; (c) about 2 mM to about 10 mM NH$_4$Cl; (d) about 10 µM to about 500 µM chloroquine; and (e) about 10 mM to about 30 mM glutamine.

In some embodiments, intracellular pH is increased by at least about 10%, at least about 20%, at least about 30%, at least about 40%, at least about 50%, at least about 60%, at least about 70%, at least about 80%, at least about 90%, at least about 100%, or more, relative to control culture conditions. In some embodiments, intracellular pH is increased by a value of at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, or more, relative to control culture conditions.

In some embodiments, the target value is a level of antibodies comprising a lysine or an arginine residue at a carboxyl terminus. In some embodiments, the target value is a level of antibodies comprising a lysine or an arginine residue at a carboxyl terminus relative to a sum of a level of antibodies comprising a lysine or an arginine residue at a carboxyl terminus and a level of antibodies not comprising a lysine or an arginine residue at a carboxyl terminus. In some embodiments, the level of antibodies comprising a lysine or an arginine residue at a carboxyl terminus relative to the sum of the level of antibodies comprising a lysine or an arginine residue at a carboxyl terminus and the level of antibodies not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises measuring a level of one or more of K0, K1, or K2 lysine variants in the population. In some embodiments, the method further comprises recording the level of one or more of K0, K1, or K2 lysine variants in a print or computer-readable medium, e.g., in a test report, Material Safety Data Sheet (MSDS) or Certificate of Testing or Certificate of Analysis (CofA).

In another aspect, the invention features a method of producing a population of recombinant antibodies, comprising: providing a target value of C-terminal variants of a recombinant antibody, providing a host cell comprising a nucleic acid encoding the recombinant antibody, culturing the host cell in a medium comprising about 2 g/L to about 50 g/L lysine, arginine and/or histidine under conditions in which the cell expresses a population of C-terminal variants of the encoded recombinant antibody; and isolating the population, wherein the population comprises the provided target value of C-terminal variants of the recombinant antibody.

In some embodiments, the medium comprises lysine, arginine, histidine, or a combination of lysine, arginine, and/or histidine, at a concentration of at least about 1.5 g/L, at least about 2 g/L, at least about 2.5 g/L, at least about 3 g/L, at least about 3.5 g/L, at least about 4 g/L, at least about 4.5 g/L, at least about 5 g/L, at least about 5.5 g/L, at least about 6 g/L, at least about 6.5 g/L, at least about 7 g/L, at least about 7.5 g/L, at least about 8 g/L, at least about 8.5 g/L, at least about 9 g/L, at least about 9.5 g/L, at least about 10 g/L, at least about 10.5 g/L, at least about 11 g/L, at least about 11.5 g/L, at least about 12 g/L, at least about 12.5 g/L, at least about 13 g/L, at least about 13.5 g/L, at least about 14 g/L, at least about 14.5 g/L, at least about 15 g/L, at least about 15.5 g/L, at least about 16 g/L, at least about 16.5 g/L, at least about 17 g/L, at least about 17.5 g/L, at least about 18 g/L, at least about 18.5 g/L, at least about 19 g/L, at least about 19.5 g/L, at least about 20 g/L, at least about 25 g/L, at least about 30 g/L, at least about 35 g/L, at least about 40 g/L, at least about 45 g/L, at least about 50 g/L, or more.

In some embodiments, the target value is a level of antibodies comprising a lysine or an arginine residue at a carboxyl terminus. In some embodiments, the target value is a level of antibodies comprising a lysine or an arginine residue at a carboxyl terminus relative to a sum of a level of antibodies comprising a lysine or an arginine residue at a carboxyl terminus and a level of antibodies not comprising a lysine or an arginine residue at a carboxyl terminus. In some embodiments, the level of antibodies comprising a lysine or an arginine residue at a carboxyl terminus relative to the sum of the level of antibodies comprising a lysine or an arginine residue at a carboxyl terminus and the level of antibodies not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises measuring a level of one or more of K0, K1, or K2 lysine variants in the population. In some embodiments, the method further comprises recording the level of one or more of K0, K1, or K2 lysine variants in a print or computer-readable medium, e.g., in a test report, Material Safety Data Sheet (MSDS) or Certificate of Testing or Certificate of Analysis (CofA).

In another aspect, the invention features a method of producing a population of recombinant antibodies, comprising: providing a target value of C-terminal variants of a recombinant antibody, providing a host cell comprising a nucleic acid encoding the recombinant antibody, culturing the host cell in a medium comprising about 0.1 g/L glucose to about 10 g/L glucose under conditions in which the cell expresses a population of C-terminal variants of the encoded recombinant antibody; and isolating the population, wherein the population comprises the provided target value of C-terminal variants of the recombinant antibody.

In some embodiments, the medium comprises glucose at a concentration of about 0.5 g/L to about 2 g/L. In some embodiments, the medium comprises glucose at a concentration of about 0.1 g/L to about 10 g/L, e.g., about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.1 g/L, about 1.2 g/L, about 1.3 g/L, about 1.4 g/L, about 1.5 g/L, about 1.6 g/L, about 1.7 g/L, about 1.8 g/L, about 1.9 g/L, about 2 g/L, about 2.1 g/L, about 2.2, g/L, about 2.3 g/L, about 2.4 g/L, about 2.5 g/L, about 2.6 g/L, about 2.7 g/L, about 2.8 g/L, about 2.9 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, or more. In some embodiments, the glucose concentration is a controlled glucose concentration.

In some embodiments, the target value is a level of antibodies comprising a lysine or an arginine residue at a carboxyl terminus. In some embodiments, the target value is a level of antibodies comprising a lysine or an arginine residue at a carboxyl terminus relative to a sum of a level of antibodies comprising a lysine or an arginine residue at a carboxyl terminus and a level of antibodies not comprising a lysine or an arginine residue at a carboxyl terminus. In some embodiments, the level of antibodies comprising a lysine or an arginine residue at a carboxyl terminus relative to the sum of the level of antibodies comprising a lysine or an arginine residue at a carboxyl terminus and the level of antibodies not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 1%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises measuring a level of one or more of K0, K1, or K2 lysine variants in the population. In some embodiments, the method further comprises recording the level of one or more of K0, K1, or K2 lysine variants in a print or computer-readable medium. e.g., in a test report. Material Safety Data Sheet (MSDS) or Certificate of Testing or Certificate of Analysis (CofA).

In another aspect, the invention features a method of producing a population of recombinant antibodies, comprising: providing a target value of C-terminal variants of a recombinant antibody, providing a host cell comprising a nucleic acid encoding the recombinant antibody, culturing the host cell in a medium comprising about 1 mM to about 50 mM $NH_4Cl$ under conditions in which the cell expresses a population of C-terminal variants of the encoded recombinant antibody; and isolating the population, wherein the population comprises the provided target value of C-terminal variants of the recombinant antibody.

In some embodiments, the medium comprises a concentration of $NH_4Cl$ of about 1 mM to about 30 mM, e.g., about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 25 mM, about 30 mM, about 40 mM, about 50 mM, or more.

In some embodiments, the target value is a level of antibodies comprising a lysine or an arginine residue at a carboxyl terminus. In some embodiments, the target value is a level of antibodies comprising a lysine or an arginine residue at a carboxyl terminus relative to a sum of a level of antibodies comprising a lysine or an arginine residue at a carboxyl terminus and a level of antibodies not comprising a lysine or an arginine residue at a carboxyl terminus. In some embodiments, the level of antibodies comprising a lysine or an arginine residue at a carboxyl terminus relative to the sum of the level of antibodies comprising a lysine or an arginine residue at a carboxyl terminus and the level of antibodies not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises measuring a level of one or more of K0, K1, or K2 lysine variants in the population. In some embodiments, the method further comprises recording the level of one or more of K0, K1, or K2 lysine variants in a print or computer-readable medium, e.g., in a test report, Material Safety Data Sheet (MSDS) or Certificate of Testing or Certificate of Analysis (CofA).

In another aspect, the invention features a method of producing a population of recombinant antibodies, comprising: providing a target value of C-terminal variants of a recombinant antibody, providing a host cell comprising a nucleic acid encoding the recombinant antibody, culturing the host cell in a medium comprising about 10 m to about 500 μm chloroquine under conditions in which the cell expresses a population of C-terminal variants of the encoded recombinant antibody; and isolating the population, wherein the population comprises the provided target value of C-terminal variants of the recombinant antibody.

In some embodiments, the medium comprises chloroquine at a concentration of about 10 μM, about 20 μM, about 30 μM, about 40 μM, about 50 μM, about 60 μM, about 70 μM, about 80 μM, about 90 μM, about 100 μM, about 110 μM, about 120 μM, about 130 μM, about 140 μM, about 150 μM, about 160 μM, about 170 μM, about 180 μM, about 190 μM, about 200 μM, about 210 μM, about 220 μM, about 230 μM, about 250 μM, about 250 μM, about 260 μM, about 270 μM, about 280 μM, about 290 μM, about 300 μM, about 310 μM, about 320 μM, about 330 μM, about 340 μM, about 350 μM, about 360 μM, about 370 μM, about 380 μM, about 390 μM, about 400 μM, about 410 μM, about 420 μM, about 430 μM, about 440 μM, about 450 μM, about 460 μM, about 470 μM, about 480 μM, about 490 μM, about 500 μM. or more.

In some embodiments, the target value is a level of antibodies comprising a lysine or an arginine residue at a carboxyl terminus. In some embodiments, the target value is a level of antibodies comprising a lysine or an arginine residue at a carboxyl terminus relative to a sum of a level of antibodies comprising a lysine or an arginine residue at a carboxyl terminus and a level of antibodies not comprising a lysine or an arginine residue at a carboxyl terminus. In some embodiments, the level of antibodies comprising a lysine or an arginine residue at a carboxyl terminus relative to the sum of the level of antibodies comprising a lysine or an arginine residue at a carboxyl terminus and the level of antibodies not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises measuring a level of one or more of K0, K1, or K2 lysine variants in the population. In some embodiments, the method further comprises recording the level of one or more of K0, K1, or K2 lysine variants in a print or computer-readable medium, e.g., in a test report, Material Safety Data Sheet (MSDS) or Certificate of Testing or Certificate of Analysis (CofA).

In another aspect, the invention features a method of producing a population of recombinant antibodies, comprising: providing a target value of C-terminal variants of a recombinant antibody, providing a host cell comprising a nucleic acid encoding the recombinant antibody, culturing the host cell in a medium comprising about 5 mM to about 80 mM glutamine under conditions in which the cell expresses a population of C-terminal variants of the encoded recombinant antibody; and isolating the population, wherein the population comprises the provided target value of C-terminal variants of the recombinant antibody.

In some embodiments, the medium comprises glutamine at a concentration of about 10 mM to about 30 mM. In other embodiments, the medium comprises glutamine at a concentration of about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, or more.

In some embodiments, the target value is a level of antibodies comprising a lysine or an arginine residue at a carboxyl terminus. In some embodiments, the target value is a level of antibodies comprising a lysine or an arginine residue at a carboxyl terminus relative to a sum of a level of antibodies comprising a lysine or an arginine residue at a carboxyl terminus and a level of antibodies not comprising a lysine or an arginine residue at a carboxyl terminus. In some embodiments, the level of antibodies comprising a lysine or an arginine residue at a carboxyl terminus relative to the sum of the level of antibodies comprising a lysine or an arginine residue at a carboxyl terminus and the level of antibodies not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises measuring a level of one or more of K0, K1, or K2 lysine variants in the population. In some embodiments, the method further comprises recording the level of one or more of K0, K1, or K2 lysine variants in a print or computer-readable medium, e.g., in a test report, Material Safety Data Sheet (MSDS) or Certificate of Testing or Certificate of Analysis (CofA).

In another aspect, the invention features a method producing a recombinant Fc-containing polypeptide, comprising: culturing a cell in a medium comprising about 1 g/L to about 50 g/L histidine under conditions in which the cell expresses a population of the recombinant antibody; isolating the population; and measuring the level of one or more of K0, K1, or K2 lysine variants of the population. In some embodiments, the Fc-containing polypeptide is an antibody.

In some embodiments, the medium comprises histidine at a concentration of at least about 1.5 g/L, at least about 2 g/L, at least about 2.5 g/L, at least about 3 g/L, at least about 3.5 g/L, at least about 4 g/L, at least about 4.5 g/L, at least about 5 g/L, at least about 5.5 g/L, at least about 6 g/L, at least about 6.5 g/L, at least about 7 g/L, at least about 7.5 g/L, at least about 8 g/L, at least about 8.5 g/L, at least about 9 g/L, at least about 9.5 g/L, at least about 10 g/L, at least about 10.5 g/L, at least about 11 g/L, at least about 11.5 g/L, at least about 12 g/L, at least about 12.5 g/L, at least about 13 g/L, at least about 13.5 g/L, at least about 14 g/L, at least about 14.5 g/L, at least about 15 g/L, at least about 15.5 g/L, at least about 16 g/L, at least about 16.5 g/L, at least about 17 g/L, at least about 17.5 g/L, at least about 18 g/L, at least about 18.5 g/L, at least about 19 g/L, at least about 19.5 g/L, at least about 20 g/L, at least about 25 g/L, at least about 30 g/L, at least about 35 g/L, at least about 40 g/L, at least about 45 g/L, at least about 50 g/L, or more In some embodiments, the level of K1 lysine variants and/or K2 lysine variants in the population is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises recording the level of K0, K1, and/or K2 lysine variants in a print or computer-readable medium, e.g., in a test report, Material Safety Data Sheet (MSDS) or Certificate of Testing or Certificate of Analysis (CofA).

In another aspect, the invention features a method producing a recombinant Fc-containing polypeptide, comprising: culturing a cell in a medium comprising about 0.1 g/L to about 10 g/L glucose under conditions in which the cell expresses a population of the recombinant antibody; isolating the population; and measuring the level of one or more of K0, K1, or K2 lysine variants of the population. In some embodiments, the Fc-containing polypeptide is an antibody.

In some embodiments, the medium comprises glucose at a concentration of about 0.5 g/L to about 2 g/L. In some embodiments, the medium comprises glucose at a concentration of about 0.1 g/L to about 10 g/L, e.g., about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.1 g/L, about 1.2 g/L, about 1.3 g/L, about 1.4 g/L, about 1.5 g/L, about 1.6 g/L, about 1.7 g/L, about 1.8 g/L, about 1.9 g/L, about 2 g/L, about 2.1 g/L, about 2.2. g/L, about 2.3 g/L, about 2.4 g/L, about 2.5 g/L, about 2.6 g/L, about 2.7 g/L, about 2.8 g/L, about 2.9 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, or more. In some embodiments, the glucose concentration is a controlled glucose concentration.

In some embodiments, the level of K1 lysine variants and/or K2 lysine variants in the population is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises recording the level of K0, K1, and/or K2 lysine variants in a print or computer-readable medium, e.g., in a test report, Material Safety Data Sheet (MSDS) or Certificate of Testing or Certificate of Analysis (CofA).

In another aspect, the invention features a method producing a recombinant Fc-containing polypeptide, comprising: culturing a cell in a medium comprising about 1 mM $NH_4Cl$ to about 50 mM $NH_4Cl$ under conditions in which the cell expresses a population of the recombinant antibody; isolating the population; and measuring the level of one or more of K0, K1, or K2 lysine variants of the population. In some embodiments, the Fc-containing polypeptide is an antibody.

In some embodiments, the medium comprises a concentration of $NH_4Cl$ of about 1 mM to about 30 mM, e.g., about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 25 mM, about 30 mM, about 40 mM, about 50 mM, or more.

In some embodiments, the level of K1 lysine variants and/or K2 lysine variants in the population is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises recording the level of K0, K1, and/or K2 lysine variants in a print or computer-readable medium, e.g., in a test report, Material Safety Data Sheet (MSDS) or Certificate of Testing or Certificate of Analysis (CofA).

In another aspect, the invention features a method producing a recombinant Fc-containing polypeptide, comprising: culturing a cell in a medium comprising about 5 mM to about 80 mM glutamine under conditions in which the cell expresses a population of the recombinant antibody; isolating the population; and measuring the level of one or more of K0, K1, or K2 lysine variants of the population. In some embodiments, the Fc-containing polypeptide is an antibody.

In some embodiments, the medium comprises glutamine at a concentration of about 10 mM to about 30 mM. In other embodiments, the medium comprises glutamine at a concentration of about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, or more.

In some embodiments, the level of K1 lysine variants and/or K2 lysine variants in the population is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises recording the level of K0, K1, and/or K2 lysine variants in a print or computer-readable medium, e.g., in a test report, Material Safety Data Sheet (MSDS) or Certificate of Testing or Certificate of Analysis (CofA).

In another aspect, the invention features a method producing a recombinant Fc-containing polypeptide, comprising: culturing a cell in a medium comprising about 10 μM to about 500 μM chloroquine under conditions in which the cell expresses a population of the recombinant antibody; isolating the population; and measuring the level of one or more of K0. K1, or K2 lysine variants of the population. In some embodiments, the Fc-containing polypeptide is an antibody.

In some embodiments, the medium comprises chloroquine at a concentration of about 10 μM, about 20 μM, about 30 μM, about 40 μM, about 50 μM, about 60 μM, about 70 μM, about 80 μM, about 90 μM, about 100 μM, about 110 μM, about 120 μM, about 130 μM, about 140 μM, about 150 μM, about 160 μM, about 170 μM, about 180 μM, about 190 μM, about 200 μM, about 210 μM, about 220 μM, about 230 μM, about 250 μM, about 250 μM, about 260 μM, about 270 μM, about 280 μM, about 290 μM, about 300 μM, about 310 μM, about 320 μM, about 330 μM, about 340 μM, about 350 μM, about 360 μM, about 370 μM, about 380 μM, about 390 μM, about 400 μM, about 410 μM, about 420 μM, about 430 μM, about 440 μM, about 450 μM, about 460 μM, about 470 μM, about 480 μM, about 490 μM, about 500 μM, or more.

In some embodiments, the level of K1 lysine variants and/or K2 lysine variants in the population is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises recording the level of K0, K1, and/or K2 lysine variants in a print or computer-readable medium, e.g., in a test report. Material Safety Data Sheet (MSDS) or Certificate of Testing or Certificate of Analysis (CofA).

In another aspect, the invention features a method of producing a preparation of recombinant Fc-containing polypeptides, comprising: culturing cells in a medium comprising one or more of: (i) about 2 g/L to about 50 g/L histidine; (ii) about 0.5 g/L glucose to about 2 g/L glucose; (iii) about 2 mM to about 10 mM NH$_4$Cl (iv) about 5 mM to about 80 mM glutamine; and (v) about 10 μM to about 500 μM chloroquine; under conditions in which the cells express recombinant antibodies; and isolating the recombinant antibodies from the cells or the medium to produce a preparation comprising a target value of K0, K1, and/or K2 lysine variants of the recombinant Fc-containing polypeptides. In some embodiments, the Fc-containing polypeptides are antibodies.

In some embodiments, the target value is a level of Fc-containing polypeptides comprising a lysine or an arginine residue at a carboxyl terminus. In some embodiments, the target value is a level of Fc-containing polypeptides comprising a lysine or an arginine residue at a carboxyl terminus relative to a sum of a level of Fc-containing polypeptides comprising a lysine or an arginine residue at a carboxyl terminus and a level of Fc-containing polypeptides not comprising a lysine or an arginine residue at a carboxyl terminus. In some embodiments, the level of Fc-containing polypeptides comprising a lysine or an arginine residue at a carboxyl terminus relative to the sum of the level of Fc-containing polypeptides comprising a lysine or an arginine residue at a carboxyl terminus and the level of Fc-containing polypeptides not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In some embodiments, the method further comprises measuring a level of one or more of K0, K1, or K2 lysine variants in the population. In some embodiments, the method further comprises recording the level of one or more of K0. K1, or K2 lysine variants in a print or computer-readable medium, e.g., in a test report, Material Safety Data Sheet (MSDS) or Certificate of Testing or Certificate of Analysis (CofA).

In one aspect, the invention features a method of producing a recombinant polypeptide, comprising: culturing a cell in a medium comprising at least about 1 g/L lysine, at least about 1 g/L arginine, or at least 1 g/L of a combination of lysine and arginine, under conditions in which the cell expresses a recombinant polypeptide.

In some embodiments, the method further comprises isolating the recombinant polypeptide. In some embodiments, the method further comprises measuring the level of lysine and/or arginine residues at the C-terminus of the isolated recombinant polypeptide. In some embodiments, the method further comprises recording the level of lysine and/or arginine residues in a print or computer-readable medium. e.g., in a test report, Material Safety Data Sheet (MSDS) or Certificate of Testing or Certificate of Analysis (CofA).

In some embodiments, the recombinant polypeptide is a recombinant antibody or a recombinant Fc fusion protein.

In another aspect, the invention features a method of producing a recombinant antibody or recombinant Fc fusion protein, comprising: culturing a cell in a medium comprising at least about 1 g/L lysine, at least about 1 g/L arginine, or at least 1 g/L of a combination of lysine and arginine, under conditions in which the cell expresses a recombinant antibody or a recombinant Fc fusion protein.

In some embodiments, the method further comprises isolating the recombinant antibody or the recombinant Fc fusion protein. In some embodiments, the method further comprises measuring a level of one or more of K0, K1, or K2 lysine variants in a preparation of the isolated recombinant antibody or the recombinant fusion protein. In some embodiments, the method further comprises recording the level of one or more of K0, K1, or K2 lysine residues in a print or computer-readable medium, e.g., in a test report, Material Safety Data Sheet (MSDS) or Certificate of Testing or Certificate of Analysis (CofA).

In another aspect, the invention features a method of producing a preparation of recombinant antibodies, comprising: culturing cells in a medium comprising at least about 1 g/L lysine, at least about 1 g/L arginine, or at least 1 g/L of a combination of lysine and arginine under conditions in which the cells express recombinant antibodies; and isolating the recombinant antibodies from the cells or the medium to produce a preparation comprising a target value of K0, K1, and/or K2 lysine variants.

In some embodiments, the method further comprises measuring the level of K0, K1, and/or K2 lysine variants in the preparation. In some embodiments, the method further comprises recording the level of K0, K1, and/or K2 lysine variants in a print or computer-readable medium, e.g., in a test report, Material Safety Data Sheet (MSDS) or Certificate of Testing or Certificate of Analysis (CofA).

In another aspect, the invention features a method of producing a preparation of recombinant antibodies, comprising: culturing cells in a medium comprising at least about 1 g/L lysine, at least about 1 g/L arginine, or at least 1 g/L of a combination of lysine and arginine under conditions in which the cells express recombinant antibodies; and isolating the recombinant antibodies from the cells or the medium to produce a preparation comprising at least about 1% of K1 and/or K2 lysine variants.

In some embodiments, the method further comprises measuring the level of K0, K1 and/or K2 lysine variants and comparing them to a reference standard (e.g., a product description in an FDA label, a Physician's Insert, a USP monograph, or an EP monograph).

In some embodiments, the method includes recording the level of K0, K1 and/or K2 lysine variants in a print or computer-readable medium, e.g., in a test report, Material Safety Data Sheet (MSDS) or Certificate of Testing or Certificate of Analysis (CofA).

In some embodiments, the method further comprises determining the level of K1, and/or K2 lysine variants in the preparation. In some embodiments, the preparation comprises at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more, of K1 and/or K2 lysine variants.

In some embodiments, the method further comprises recording the level of K0, K1, and/or K2 lysine variants in a print or computer-readable medium, e.g., in a test report, Material Safety Data Sheet (MSDS) or Certificate of Testing or Certificate of Analysis (CofA).

In another aspect, the invention features a method of producing a preparation of recombinant antibodies having a target value of one or more of K0. K1, or K2 lysine variants, comprising: culturing cells in a medium comprising lysine and/or arginine under conditions in which the cells express recombinant antibodies; measuring a level of one or more of K0, K1, or K2 lysine variants in the culture; and isolating the recombinant antibodies from the cells or the medium to produce a preparation of the recombinant antibodies when the level of one or more of K0, K1, or K2 lysine variants in the culture is a target value.

In some embodiments, the method further comprises recording the level of K0, K1, and/or K2 lysine variants in a print or computer-readable medium, e.g., in a test report. Material Safety Data Sheet (MSDS) or Certificate of Testing or Certificate of Analysis (CofA).

In another aspect, the invention features a method of decreasing a level of K0 lysine variants and/or increasing a level of one or more of K1 or K2 lysine variants in a preparation of recombinant antibodies, comprising: culturing cells in a medium comprising an amount of lysine, arginine, and/or a combination of lysine and arginine that is more than an amount of lysine, arginine, and/or a combination of lysine and arginine in a standard medium, wherein the cells are cultured under conditions in which the cells express recombinant antibodies; and isolating the recombinant antibodies, thereby decreasing the level of K0 lysine variants and/or increasing the level of one or more of K1 or K2 lysine variants in the preparation relative to a preparation of recombinant antibodies produced from cells cultured in a standard medium.

In another aspect, the invention features a method of decreasing a level of K0 lysine variants and/or increasing a level of one or more of K1 or K2 lysine variants in a preparation of recombinant antibodies, comprising: culturing cells in a medium comprising at least about 1 g/L lysine, at least about 1 g/L arginine, or at least 1 g/L of a combination of lysine and arginine under conditions in which the cells express recombinant antibodies; and isolating the recombinant antibodies, thereby decreasing the level of K0 lysine variants and/or increasing the level of one or more of K1 or K2 lysine variants in the preparation relative to a preparation of recombinant antibodies not produced using a medium comprising at least about 1 g/L lysine, at least about 1 g/L arginine, or at least 1 g/L of a combination of lysine and arginine.

In another aspect, the invention features a method of culturing cells producing a recombinant antibody, comprising: growing cells in a medium comprising at least about 1 g/L lysine, at least about 1 g/L arginine, or at least 1 g/L of a combination of lysine and arginine under conditions in which the cells express a recombinant antibody.

In some embodiments, the method further comprises monitoring a level of one or more of K0, K1, or K2 lysine variants in the culture. In some embodiments, the method further comprises removing the cells from the culture when the level of one or more of K0. K1, or K2 lysine variants reaches a target value.

In another aspect, the invention features a recombinant polypeptide, such as a recombinant antibody, produced by a method described herein.

In another aspect, the invention features a cell culture medium comprising at least about 1 g/L lysine, at least about 1 g/L arginine, or at least 1 g/L of a combination of lysine and arginine.

In another aspect, the invention features a cell culture comprising: cells expressing recombinant antibodies; and a medium comprising at least about 1 g/L lysine, at least about 1 g/L arginine, or at least 1 g/L of a combination of lysine and arginine.

In some embodiments, the culture comprises a target value of one or more of K0. K1, or K2 lysine variants.

In some embodiments, the culture is a batch culture, a continuous culture, or a fed-batch culture.

In another aspect, the invention features a bioreactor comprising a cell culture described herein.

In some aspects described herein, the medium comprises lysine (e.g., L-lysine), arginine (e.g., L-arginine), or a combination of lysine (e.g., L-lysine) and arginine (e.g., L-arginine), in an amount of at least about 1.5 g/L, at least about 2 g/L, at least about 2.5 g/L, at least about 3 g/L, at least about 3.5 g/L, at least about 4 g/L, at least about 4.5 g/L, at least about 5 g/L, at least about 5.5 g/L, at least about 6 g/L, at least about 6.5 g/L, at least about 7 g/L, at least about 7.5 g/L, at least about 8 g/L, at least about 8.5 g/L, at least about 9 g/L, at least about 9.5 g/L, at least about 10 g/L, at least about 10.5 g/L, at least about 11 g/L, at least about 11.5 g/L, at least about 12 g/L, at least about 12.5 g/L, at least about 13 g/L, at least about 13.5 g/L, at least about 14 g/L, at least about 14.5 g/L, at least about 15 g/L, at least about 15.5 g/L, at least about 16 g/L, at least about 16.5 g/L, at least about 17 g/L, at least about 17.5 g/L, at least about 18 g/L, at least about 18.5 g/L, at least about 19 g/L, at least about 19.5 g/L, at least about 20 g/L, at least about 25 g/L, at least about 30 g/L, at least about 35 g/L, at least about 40 g/L, at least about 45 g/L, at least about 50 g/L, or more.

In other aspects, the medium comprises lysine (e.g., L-lysine), arginine (e.g., L-arginine), or a combination of lysine (e.g., L-lysine) and arginine (e.g., L-arginine), in an amount of at least about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 125 mM, about 150 mM, about 200 mM, about 250 mM, about 300 mM, about 350 mM, about 400 mM, about 450 mM, about 500 mM, or more.

In another aspect, the invention features a method of increasing a level of K0 lysine variants and/or decreasing a level of one or more of K1 or K2 lysine variants in a preparation of recombinant antibodies, comprising: culturing cells in a medium comprising an amount of lysine, arginine, and/or a combination of lysine and arginine that is less than an amount of lysine, arginine, and/or a combination of lysine and arginine in a standard medium, wherein the cells are cultured under conditions in which the cells express recombinant antibodies; and isolating the recombinant antibodies, thereby increasing the level of K0 lysine variants and/or decreasing the level of one or more of K1 or K2 lysine variants in the preparation relative to a preparation of recombinant antibodies produced from cells cultured in a standard medium.

In some aspects described herein, the method further comprises monitoring the amount of lysine, arginine, histidine, glucose, $NH_4Cl$, chloroquine, and/or glutamine in the medium during the culturing step, e.g., at least once, twice, three times or more during the culturing step.

In some aspects described herein, the target value is a level set forth in a reference standard, such as a product specification or a quality criterion for a pharmaceutical preparation containing the recombinant antibody preparation. For example, the product specification is a product description in an FDA label, a Physician's Insert, a USP monograph, or an EP monograph.

In particular embodiments, the target value is a level of K0, K1, and/or K2 lysine variants in a preparation of corresponding recombinant antibodies.

In another aspect, the invention features a method of producing a preparation of recombinant antibodies, comprising: culturing cells in a medium comprising one or more of: (i) about 2 g/L to about 50 g/L histidine; (ii) about 0.5 g/L glucose to about 2 g/L glucose; (iii) about 2 mM to about 10 mM $NH_4Cl$; (iv) about 5 mM to about 80 mM glutamine; and (v) about 10 µM to about 500 µM chloroquine; under conditions in which the cells express recombinant antibodies; isolating the recombinant antibodies from the cells or the medium to produce a preparation; measuring the level of K0, K1, and/or K2 lysine variants of the recombinant antibodies in the preparation; and formulating the preparation the preparation into a drug product if the level of K0, K1, and/or K2 lysine variants is a target value.

In some embodiments, the target value is a level of antibodies comprising a lysine or an arginine residue at a carboxyl terminus. In some embodiments, the target value is a level of antibodies comprising a lysine or an arginine residue at a carboxyl terminus relative to a sum of a level of antibodies comprising a lysine or an arginine residue at a carboxyl terminus and a level of antibodies not comprising a lysine or an arginine residue at a carboxyl terminus. In some embodiments, the level of antibodies comprising a lysine or an arginine residue at a carboxyl terminus relative to the sum of the level of antibodies comprising a lysine or an arginine residue at a carboxyl terminus and the level of antibodies not comprising a lysine or an arginine residue at a carboxyl terminus is about 0.1, about 0.2, about 0.3, about 0.4, about 0.5, about 0.6, about 0.7, about 0.8, about 0.9, or about 1.

In some embodiments, the target value is a level of heavy chains in the population comprising a C-terminal lysine or arginine. In some embodiments, the target value is a level of heavy chains having a C-terminal lysine or arginine in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more. In some embodiments, the target value is a level of K1 lysine variants and/or K2 lysine variants in the population. In some embodiments, the target value is a level of K1 lysine variants and/or K2 lysine variants in the population of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more.

In another aspect, the invention features a method of manufacturing a pharmaceutical antibody preparation, comprising: providing a target value of C-terminal lysine variants for a therapeutic recombinant antibody, providing a host cell comprising a nucleic acid encoding a light chain and a heavy chain of a recombinant antibody, culturing the host cell under conditions (i) in which the cell expresses the encoded light chain and heavy chain to form the recombinant antibody and (ii) which increase the intracellular pH of the cell, isolating a population of the therapeutic recombinant antibody from the cell or cell culture, and formulating the isolated population into a pharmaceutical drug product if the population comprises the provided target value of C-terminal lysine variants, thereby manufacturing a pharmaceutical antibody preparation.

In some embodiments, the target value of C-terminal lysine variants is a preselected level of C-terminal lysine-containing heavy chains relative to the total heavy chains in the population. In some embodiments, the target value of C-terminal lysine variants is a preselected level of K1 lysine variants and/or K2 lysine variants in the population.

In some aspects described hemin, the conditions in which cells (e.g., mammalian cells) express recombinant polypeptides or recombinant antibodies comprise (i) a medium having a pH of about 6, about 6.5, about 6.6, about 6.7, about 6.8, about 6.9, about 7, about 7.1, about 7.2, about 7.3, about 7.4, about 7.5, or about 8: (ii) a temperature of about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C.; and/or (iii) a culture volume of about 100 mL, about 200 mL, about 300 mL, about 400 mL, about 500 mL, about 600 mL, about 700 mL, about 800 mL, about 900 mL, about 1 L, about 2 L, about 3 L, about 5 L, about 10 L, about 20 L, about 30 L, about 40 L, about 50 L, about 100 L, about 200 L, about 300 L, about 400 L, about 500 L, about 600 L, about 700 L, about 800 L, about 900 L, about 1000 L, or more.

In some aspects described herein, the cells are mammalian cells. In certain embodiments, the mammalian cells are CHO, Vero, BHK, HeLa, COS, MDCK, or HEK-293 cells.

In some aspects described herein, the recombinant antibody is abciximab, adalimumab, alemtuzumab, basiliximab, bevacizumab, cetuximab, certolizumab, daclizumab, eculizumab, efalizumab, gemtuzunmab, ibritumorrmab, inflixinab, muromrionab, natalizuinab, omalizumab, palivizumab, panitumumab, ranibizumab, rituximab, tositumomab, or trastuzumab.

In some aspects described herein, the polypeptide is a fusion protein. In certain embodiments, the fusion protein is alefacept, abatacept, etanercept, rilonacept, or denileukin diftitox.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

FIG. 1 is a graphic representation of the levels of K1 and K2 lysine residues in a preparation of a model antibody from cells grown in a control process, in a process supplemented with 10 g/L lysine, in a process supplemented with 10 g/L arginine, compared to levels of K1 and K2 lysine residues in a preparation of Humira®.

DETAILED DESCRIPTION

The inventors have discovered that polypeptides (e.g., antibodies) having targeted levels of carboxyl terminal (C-terminal) lysine or arginine residues can be produced from cells cultured in a medium having sufficient levels of lysine, arginine, and/or agents that change intracellular pH. Surprisingly, culturing the cells under such conditions does not affect cell growth, cell viability, or titer. The present disclosure encompasses polypeptides (e.g., antibodies) having targeted levels of C-terminal lysine and/or arginine residues, methods of making such polypeptides (e.g., antibodies), and methods of using such polypeptides (e.g., antibodies).

Definitions

As used herein, "purified" (or "isolated") refers to a nucleic acid sequence (e.g., a polynucleotide) or an amino acid sequence (e.g., a polypeptide) that is substantially free of other components. In some embodiments, a purified polynucleotide or purified polypeptide is removed or separated from other components present in its natural environment. For example, an isolated polypeptide is one that is separated from other components of a cell in which it was produced (e.g., the endoplasmic reticulum or cytoplasmic proteins and RNA). An isolated polynucleotide is one that is separated from other nuclear components (e.g., histones) and/or from upstream or downstream nucleic acid sequences. An isolated nucleic acid sequence or amino acid sequence can be at least 60% free, or at least 75% free, or at least 90% free, or at least 95% free from other components present in natural environment of the indicated nucleic acid sequence or amino acid sequence.

As used herein, "polynucleotide" (or "nucleotide sequence" or "nucleic acid molecule") refers to an oligonucleotide, nucleotide, or polynucleotide, and fragments or portions thereof, and to DNA and RNA of genomic or synthetic origin, which may be single- or double-stranded, and represent the sense or anti-sense strand.

As used herein, "polypeptide" (or "amino acid sequence" or "protein") refers to an oligopeptide, peptide, polypeptide, or protein sequence, and fragments or portions thereof, and to naturally occurring or synthetic molecules. "Amino acid sequence" and like terms, such as "polypeptide" or "protein", are not meant to limit the indicated amino acid sequence to the complete, native amino acid sequence associated with the recited protein molecule.

The articles "a" and "an" are used herein to refer to one or to more than one (i.e., to at least one) of the grammatical object of the article. By way of example, "an element" means one element or more than one element.

The term "pharmaceutically effective amount" or "therapeutically effective amount" refers to an amount (e.g., dose) effective in treating a patient, having a disorder or condition described herein. It is also to be understood herein that a "pharmaceutically effective amount" may be interpreted as an amount giving a desired therapeutic effect, either taken in one dose or in any dosage or route, taken alone or in combination with other therapeutic agents.

The term "treatment" or "treating", as used herein, refers to administering a therapy in an amount, manner, and/or mode effective to improve a condition, symptom, or parameter associated with a disorder or condition or to prevent or reduce progression of a disorder or condition, to a degree detectable to one skilled in the art. An effective amount, manner, or mode can vary depending on the subject and may be tailored to the subject.

The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG. IgE. IgD, IgM (as well as subtypes thereof). The light chains of the immunoglobulin can be of types kappa or lambda. In some embodiments, an antibody includes an Fc region. In some embodiments, an antibody is a therapeutic antibody.

As used herein, the term "constant region" refers to a polypeptide that corresponds to, or is derived from, one or more constant region immunoglobulin domains of an antibody. A constant region can include any or all of the following immunoglobulin domains: a CH1 domain, a hinge region, a CH2 domain, a CH3 domain (derived from an IgA, IgD, IgG, IgE, or IgM), and a CH4 domain (derived from an IgE or IgM).

As used herein, the term "Fc region" refers to a polypeptide comprising the constant region of an antibody excluding the first constant region immunoglobulin domain. "Fc region" refers to the last two constant region immunoglobulin domains of IgA. IgD, and IgG, and the last three constant region immunoglobulin domains of IgE and IgM, and may also include part or all of the flexible hinge N-terminal to these domains. For IgG, "Fc region" comprises immunoglobulin domains Cgamma2 (Cγ2) and Cgamma3 (Cγ3) and the lower part of the hinge between Cgamma1 (Cγ1) and Cγ2. Although the boundaries of the Fc region may vary, the human IgG heavy chain Fc region is usually defined to comprise residues starting at T223 or C226 or P230, to its carboxyl-terminus, wherein the numbering is according to the EU index as in Kabat et al. (1991. NIH Publication 91-3242, National Technical Information Services, Springfield, VA). For IgA, the Fc region comprises immunoglobulin domains Calpha2 (Cα2) and Calpha3 (Cα3) and the lower part of the hinge between Calpha1 (Cα1) and Cα2.

As used herein, the term "Fc-containing polypeptide" refers to a polypeptide comprising a dimer of two polypeptides containing Fc regions, such as an intact antibody or Fc-receptor fusion protein.

As used herein, the term "Fc region variant" refers to an analog of an Fc region that possesses one or more Fc-mediated activities described herein. This term includes Fc regions comprising one or more amino acid modifications relative to a wild type or naturally existing Fc region. For example, variant Fc regions can possess at least about 50% homology, at least about 75% homology, at least about 80% homology, at least about 85%, homology, at least about 90% homology, at least about 95% homology, or more, with a naturally existing Fc region. Fc region variants also include Fc regions comprising one or more amino acid residues added to or deleted from the N- or C-terminus of a wild type Fc region.

As used herein, the terms "coupled", "linked", "joined", "fused", and "fusion" are used interchangeably. These terms refer to the joining together of two more elements or components by whatever means, including chemical conjugation or recombinant means.

The terms "overexpress," "overexpression" or "overexpressed" interchangeably refer to a protein that is transcribed and translated or to a nucleic acid that is transcribed at a detectably greater level than the level in a control cell. The term includes expression due to transcription, post transcriptional processing, translation, post-translational processing, cellular localization (e.g., organelle, cytoplasm, nucleus, cell surface), and RNA and protein stability, as compared to a control cell. Overexpression can be detected using conventional techniques, e.g., for detecting mRNA (i.e., RT-PCR, PCR, hybridization) or proteins (i.e., ELISA, immunohistochemical techniques). Overexpression can be expression in an amount greater than about 10%, 20%, 30%, 40%, 50%, 60%, 70%, 80%, 90% or more compared to the expression in a control cell. In certain instances, overexpression is 1-fold, 2-fold, 3-fold, 4-fold, or more, higher level of transcription or translation compared to expression in a control cell.

As used herein, "C-terminal variants" of a polypeptide (e.g., an antibody or an Fc-containing polypeptide) are versions of such polypeptide (e.g., antibody or Fc-containing polypeptide) that differ in amino acid sequence only by the presence or absence of a particular amino acid residue at their carboxyl termini. In some embodiments, "C-terminal variants" of a polypeptide differ only by the presence or absence of a lysine or arginine residue at their C-termini. In some embodiments, "C-terminal variants" of an antibody or Fc-containing polypeptide are K0 lysine variants, K1 lysine variants, K2 lysine variants. R0 arginine variants, R1 arginine variants, and/or R2 arginine variants.

As used herein, "K0 lysine variant", "K1 lysine variant", and "K2 lysine variant" of an antibody or an Fc-containing polypeptide are versions of such antibody or Fc-containing polypeptide (e.g., polypeptide including an Fc dimer, e.g., an intact antibody) that differ in amino acid sequence only by the presence or absence of a lysine residue at their heavy chain carboxyl termini. A "K0 lysine variant" does not have a lysine residue at either heavy chain C-terminus. A "K1 lysine variant" has a lysine residue at one heavy chain C-terminus. A "K2 lysine variant" has a lysine residue at each heavy chain C-terminus.

As used herein, "R0 arginine variant", "R1 arginine variant", and "R2 arginine variant" of an antibody or Fc-containing polypeptide are versions of such antibody or Fc-containing polypeptide (e.g., polypeptide including an Fc dimer, e.g., an intact antibody) that differ in amino acid sequence only by the presence or absence of an arginine residue at their heavy chain carboxyl termini. An "R0 arginine variant" does not have an arginine residue at either heavy chain C-terminus. An "R1 arginine variant" has an arginine residue at one heavy chain C-terminus. An "R2 arginine variant" has an arginine residue at each heavy chain C-terminus.

As used herein, "preparation" in the context of polypeptides, fusion proteins, antibodies, or Fc-containing polypeptides, refers to a set of individual polypeptides, fusion proteins, antibodies, or Fc-containing polypeptides, respectively, each of which comprises a particular amino acid sequence. In some embodiments, a preparation includes C-terminal variants of such polypeptides, fusion proteins, antibodies, or Fc-containing polypeptides. In some embodiments, individual polypeptides, fusion proteins, antibodies, or Fc-containing polypeptides within a preparation have identical amino acid sequences but differ in the presence or absence of a particular amino acid residue (e.g., a lysine residue or an arginine residue) at a carboxyl terminus. For example, a "preparation of antibodies" refers to a set of antibodies that includes one or more C-terminal variants. In some embodiments, a "preparation of antibodies" includes one or more of K0 lysine variants, K1 lysine variants, K2 lysine variants, R0 arginine variants, R1 arginine variants, and R2 arginine variants.

As used herein, a "target value" is a predetermined level of one or more C-terminal variants, such as K0 lysine variants, K1 lysine variants, K2 lysine variants, R0 arginine variants. R1 arginine variants, and/or R2 arginine variants. In some embodiments, a target value is an absolute value. In some embodiments, a target value is a relative value. In some embodiments, a target value is a level of C-terminal lysine-containing polypeptide relative to the sum of levels of C-terminal lysine-containing polypeptides and C-terminal lysine-free polypeptides, e.g., detected in a population of such polypeptides.

In some embodiments, a "target value" is a level of heavy chains in a preparation of an Fc-containing polypeptide (e.g., antibody) comprising a C-terminal lysine or arginine. In some embodiments, a target value is a level of heavy chains having a C-terminal lysine or arginine in such a preparation of greater than about 5%, greater than about 10%, greater than about 15%, or greater than about 20%, or more.

In some embodiments, a "target value" is a level of K1 lysine variants and/or K2 lysine variants in a preparation of isolated recombinant Fc-containing polypeptides (e.g., antibodies). In some embodiments, a target value is a level of K1 lysine variants and/or K2 lysine variants in such a preparation of greater than about 5%, greater than about 10%, greater than about 15%, or greater than about 20%, or more.

As used herein, a "corresponding recombinant antibody" means a recombinant antibody that is the same recombinant antibody as a particular antibody but produced by a different recombinant method. For example, a corresponding recombinant antibody can be a bioequivalent or a biosimilar antibody.

Carboxypeptidases

C-terminal lysine or arginine residues are often absent in proteins isolated from mammalian cell cultures, even though their presence may be expected on the basis of gene sequence. This discrepancy often results from the activity of one or more carboxypeptidases. The carboxypeptidase family of exopeptidases constitute a diverse group of enzymes that hydrolyze carboxyl-terminal amide bonds in polypeptides. Carboxypeptidase B is a zinc-containing exopeptidase catalyzing a hydrolytic release of the C-terminal basic amino acid residues of arginine and lysine from peptides and proteins. Other mammalian carboxypeptidases besides carboxypeptidase B that specifically remove terminal basic amino acids include carboxypeptidase H (also known as enkephalin convertase or carboxypeptidase E (Frickler et al., *J. Mol. Endocrinol.*, 3: 666-673 (1989); Manser et al., *Biochem. J.*, 267: 517-525 (1990)), carboxypeptidase M (EC 3.4.17.12) (Tan et al., *J. Biol. Chem.*, 264: 13165-13170 (1989)), carboxypeptidase N (Tan et al., *J. Biol. Chem.*, 265: 13-19 (1990)), carboxypeptidase U, carboxypeptidase D, carboxypeptidase R, carboxypeptidase Z. and SCPEP1 (Reznik et al., *CMLS, Cell. Mol. Life Sci.* 58:1790-1804 (2001)).

Agents for C-Terminal Modification of Polypeptides

In some embodiments, an activator or an inhibitor of a carboxypeptidase is used to produce targeted levels of C-terminal variants of polypeptides (e.g., antibodies). Activators and inhibitors of various carboxypeptidases are known. Exemplary, nonlimiting activators for carboxypeptidase E and/or M include $Co^{2+}$, $Zn^{2+}$, $NiCl_2$, $Na_2SO_4$, $KCl$, $NaNO_3$, $NaCl$, and $KNO_3$. Inhibitors for these enzymes include, but are not limited to, 1,10-phenanthroline; 4-chloromercuriphenylsulfonate; aminopropylmercaptosuccinic acid; arginine; $CdCl_2$ (Cd compounds); $CuCl_2$; EDTA; $FeSO_4$; Guanidinoethylmercaptosuccinic acid (GEMSA); $HgCl_2$; Leu-enkephalin; luteinizing hormone-releasing hormone; lysine; Met-enkephalin; Met-Enkephalin-Arg-Gly-Leu; oxytocin; p-chloromercuriphenyl sulfonate; Substance P; sulfhydryl reagents; thyrotropin-releasing hormone; [Leu5]Enkephalin-Arg6; [Met5]Enkephalin-Arg6; and Met-Enkephalin-Arg6-Phe7. Particular inhibitors useful in the present disclosure are lysine and arginine, e.g., L-lysine, D-lysine. L-arginine. D-arginine, and derivatives and salts thereof.

In some embodiments, an agent capable of directly or indirectly modifying pH (e.g., intracellular pH of a cell described herein) ("pH modifying agent") is used to produce targeted levels of C-terminal variants of polypeptides (e.g., antibodies). Without wishing to be bound by theory, it is believed that modifying, e.g., increasing, intracellular pH can modify, e.g., increase, levels of C-terminal lysine and/or arginine residues on polypeptides (e.g., antibodies) by directly or indirectly modifying one or more mechanisms involved in regulation of C-terminal lysine and/or arginine residues. Such a mechanism can include, or can be independent of, carboxypeptidase activity. For example, without wishing to be bound by theory, it is believed that increasing pH of intracellular compartments involved in the secretory pathway can increase levels of C-terminal lysine and/or arginine residues of a polypeptide (e.g., antibody). Accordingly, in some embodiments, a pH modifying agent that can increase pH in one or more compartments of secretory pathway of a cell (e.g., ER, Golgi, secretory vesicle) is used to increase levels of C-terminal lysine and/or arginine residues of a polypeptide (e.g., an antibody), e.g., to a targeted level.

Such pH modifying agents include, without limitation, ammonium salts (e.g., ammonium nitrate, ammonium carbonate, ammonium acetate, ammonium methanesulfonate, ammonium tolylsulfonate, ammonium chloride, ammonium bromide, ammonium sulfate, or ammonium phosphate), basic amino acids (e.g., lysine, arginine, and/or histidine), polar amino acids (e.g., glutamine, asparagine, serine, or threonine), glucose, chloroquine, methylamine, tributylamine, benzylamine, and triethylamine.

In some embodiments, an activator or an inhibitor of a carboxypeptidase is also a pH modifying agent. For example, lysine and/or arginine can inhibit a carboxypeptidase and can also increase intracellular pH. Without wishing to be bound by theory, such agents can increase levels of C-terminal lysine and/or arginine residues of a polypeptide (e.g., antibody), to a targeted level, by inhibiting a carboxypeptidase, by increasing intracellular pH, or both.

As described herein, carboxypeptidase activators, carboxypeptidase inhibitors, and/or pH modifying agents, are used to produce targeted levels of C-terminal variants of polypeptides (e.g., antibodies). In particular instances, K0 lysine variants, K1 lysine variants, K2 lysine variants, R0 arginine variants. R1 arginine variants, and/or R2 arginine variants of antibodies are produced. For example, carboxypeptidase inhibitors (e.g., arginine and/or lysine), carboxypeptidase activators, and/or pH modifying agents are used to prepare targeted levels of K0 lysine variants, K1 lysine variants, K2 lysine variants, R0 arginine variants, R1 arginine variants, and/or R2 arginine variants.

Cells

Any host cell that can be used to express a polypeptide of interest (e.g., an antibody) can be used in the methods described herein. The cells can contain a recombinant nucleic acid sequence, e.g., a gene, that encodes a polypeptide of interest (e.g., an antibody). For example, useful cells can express a recombinant polypeptide. Recombinant expression of a gene encoding a polypeptide, can include construction of an expression vector containing a polynucleotide that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then cultured by conventional techniques to produce polypeptide. A variety of host expression vector systems can be used (see, e.g., U.S. Pat. No. 5,807,715). Such host-expression systems can be used to produce polypeptides (e.g., antibodies) and, where desired, subsequently purified. Such host expression systems include, but are not limited to, yeast (e.g., *Saccharomyces* and *Pichia*) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing polypeptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For expression in mammalian host cells, viral-based expression systems can be utilized (see, e.g., Logan et al., 1984, *Proc. Natl. Acad. Sci. USA* 8:355-359). The efficiency of expression can be enhanced by the inclusion of appropriate transcription enhancer elements, transcription terminators, etc. (see, e.g., Bittner et al., 1987, *Methods in Enzymol.* 153:516-544).

In addition, a host cell strain can be chosen that modulates the expression of the inserted sequences, or modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the polypeptide (e.g., antibody) expressed. Such cells include, for example, established mammalian cell lines and insect cell lines, animal cells, fungal cells, and yeast cells. Mammalian host cells include, but are not limited to, CHO, Vero, BHK, HeLa, COS, MDCK, HEK-293, NTH-3T3, W138, BT483. Hs578T. HTB2, BT20, T47D, NS0 (a murine myeloma cell line that does not endogenously produce any immunoglobulin chains). CRL7030, HsS78Bst cells, PER.C6, SP2/0-Agl4, and hybridoma cells. Additional, nonliniting examples of animal or mammalian host cells include Chinese hamster ovary cells (CHO), such as CHO-K1 (ATCC CCL-61), DG44 (Chasin et al., 1986, *Som. Cell Molec. Genet.*, 12:555-556; and Kolkekar et al., 1997, *Biochem.*, 36:10901-10909). CHO-DXB11 (G. Urlaub and L. A. Chasin, 1980 *Proc. Natl. Acad. Sci.*, 77: 4216-4220. L. H. Graf, and L. A. Chasin 1982. Molec. Cell. Biol., 2: 93-96). CHO-K1 Tet-On cell line (Clontech), CHO designated ECACC 85050302 (CAMR, Salisbury, Wiltshire, UK). CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/–DHFR, Urlaub and Chasin, 1980, *Proc. Natl. Acad. Sci. USA,* 77:4216), and dp12.CHO cells (U.S. Pat. No. 5,721,121); monkey kidney CV1 cells transformed by SV40 (COS cells, COS-7. ATCC CRL-1651); human embryonic kidney cells (e.g., 293 cells, or 293 cells subcloned for growth in suspension culture, Graham et al., 1977, *J. Gen. Virol.*, 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4. Mather, 1980. *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TR1 cells (Mather, 1982, *Ann. NY Acad. Sci.*, 383:44-68); MCR 5 cells; and FS4 cells.

For long-term, high-yield production of recombinant proteins, host cells are engineered to stably express a polypeptide (e.g., antibody). Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone.

Once a polypeptide described herein (e.g., an antibody described herein) has been produced by recombinant expression, it may be purified by any method known in the art for purification, for example, by chromatography (e.g., ion exchange, affinity, and sizing column chromatography), centrifugation, differential solubility, or by any other standard technique for the purification of proteins. For example, an antibody can be isolated and purified by appropriately selecting and combining affinity columns such as Protein A column with chromatography columns, filtration, ultra filtration, salting-out and dialysis procedures (see *Antibodies: A Laboratory Manual*, Ed Harlow, David Lane, Cold Spring Harbor Laboratory, 1988). Further, as described herein, a polypeptide (e.g., an antibody) can be fused to heterologous polypeptide sequences to facilitate purification. Polypeptides having desired sugar chains can be separated with a lectin column by methods known in the art (see, e.g., WO 02/30954).

In accordance with the present disclosure, there may be employed conventional molecular biology, microbiology, and recombinant DNA techniques within the skill of the art. Such techniques are described in the literature (see, e.g., Sambrook. Fritsch & Maniatis, *Molecular Cloning: A Laboratory Manual*, Second Edition (1989) Cold Spring Harbor Laboratory Press, Cold Spring Harbor, N.Y.; *DNA Cloning: A Practical Approach*. Volumes I and 11 (D. N. Glover ed. 1985); Oligonucleotide Synthesis (M. J. Gait ed. 1984); *Nucleic Acid Hybridization* (B. D. Hames & S. J. Higgins eds. (1985)); *Transcription And Translation* (B. D. Hames &

S. J. Higgins, eds. (1984)); *Animal Cell Culture* (R. I. Freshney, ed. (1986)); *Immobilized Cells and Enzymes* (TRL Press, (1986)); B. Perbal, *A Practical Guide To Molecular Cloning* (1984); F. M. Ausubel et al. (eds.), *Current Protocols in Molecular Biology*. John Wiley & Sons, Inc. (1994).

Culture Methods

In general, targeted levels of C-terminal variants of polypeptides (e.g., antibodies), can be produced by cells cultured in media that contains one or more carboxypeptidase activators, carboxypeptidase inhibitors, and/or pH modifying agents. For example, for producing a preparation of C-terminal variants of a polypeptide (e.g., antibody) having a reduced level of C-terminal lysine and/or arginine residues, cells expressing such polypeptides can be cultured in a medium that includes an elevated level of a carboxypeptidase activator, a reduced level of a carboxypeptidase inhibitor (e.g., arginine or lysine), and/or that includes an agent that reduces intracellular pH. In some embodiments for producing a preparation of C-terminal variants of polypeptides (e.g., antibodies) having a higher level of C-terminal lysine and/or arginine residues, cells expressing such polypeptides can be cultured in a medium that contains an elevated level of a carboxypeptidase inhibitor (e.g., arginine or lysine), a reduced level of a carboxypeptidase activator, and/or that includes an agent that increases intracellular pH.

As used herein, an "elevated level" of a component means a higher concentration of a component than is present in a standard medium, and/or that is present in a medium in which a polypeptide is produced. In some embodiments, a component is not present in a standard medium, and an "elevated level" is any amount of such component. A medium can include an elevated level of a component initially (i.e., at the start of a culture), or a starting medium can be supplemented with a component to achieve an elevated level of the component at a particular time or times during culturing. For example, the starting medium can include at least about 2 g/L arginine, at least about 2 g/L lysine, or at least about 2 g/L of a combination of arginine and lysine.

As used herein, a "reduced level" of a component means a lower concentration of a component than is present in a standard medium, and/or that is present in a medium in which a polypeptide is produced. A medium can include a reduced level of a component initially (i.e., at the start of a culture), a starting medium can be diluted at a particular time or times during culturing to reduce the level of a component, or a starting medium can be replaced with a medium having a reduced level of a component at a particular time or times during culturing.

In some embodiments, a polypeptide (e.g., antibody) preparation having targeted values of C-terminal variants is produced by culturing a cell expressing the polypeptide (e.g., antibody) under conditions that increase intracellular pH of the cell, e.g., that increase pH of one or more secretory compartments of the cell described herein. Intracellular pH can be measured using known methods, e.g., by using a pH-sensitive green fluorescent protein (see. e.g., Tomkins et al., Am. J. Phys. Cell Physiol. 283:C429-37 (2002); Blackmore et al., J. Physiol. 531:605-617 (2001); Miesenbock et al., Nature 394:192-195 (1998)). In some embodiments, intracellular pH is increased using a pH modulating agent, e.g., an agent described herein. In some embodiments, intracellular pH1 (e.g., pH of a secretory compartment) is increased by at least about 10%, at least about 20%, at least about 30%, at least about 40%, at least about 50%, at least about 60%, at least about 70%, at least about 80%, at least about 90%, at least about 100%, or more. In some embodiments, intracellular pH (e.g., pH of a secretory compartment) is increased by a value of at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, or more.

In some embodiments, a polypeptide (e.g., antibody) preparation having targeted values of C-terminal variants is produced by culturing a cell expressing the polypeptide (e.g., antibody) in a medium having an elevated level of an ammonium salt (e.g., $NH_4Cl$). In some embodiments, a medium contains $NH_4Cl$ at a concentration of about 1 mM to about 30 mM, e.g., about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 25 mM, about 30 mM, about 40 mM, about 50 mM, or more.

In some embodiments, a polypeptide (e.g., antibody) preparation having targeted values of C-terminal variants is produced by culturing a cell expressing the polypeptide (e.g., antibody) in a medium having an elevated level of chloroquine. In some embodiments, a medium contains chloroquine at a concentration of about 10 μM to about 500 μM, e.g., about 10 μM, about 20 μM, about 30 μM, about 40 μM, about 50 μM, about 60 μM, about 70 μM, about 80 μM, about 90 μM, about 100 μM, about 110 μM, about 120 μM, about 130 μM, about 140 μM, about 150 μM, about 160 μM, about 170 μM, about 180 μM, about 190 μM, about 200 μM, about 210 μM, about 220 μM, about 230 μM, about 250 μM, about 250 μM, about 260 μM, about 270 μM, about 280 μM, about 290 μM, about 300 μM, about 310 μM, about 320 μM, about 330 μM, about 340 μM, about 350 μM, about 360 μM, about 370 μM, about 380 μM, about 390 μM, about 400 μM, about 410 μM, about 420 μM, about 430 μM, about 440 μM, about 450 μM, about 460 μM, about 470 μM, about 480 μM, about 490 μM, about 500 μM, or more.

In some embodiments, a polypeptide (e.g., antibody) preparation having targeted values of C-terminal variants of such polypeptide (e.g., antibody) is produced by culturing a cell expressing the polypeptide (e.g., antibody) in a medium having an elevated level of methylamine, tributylamine, benzylamine, and/or triethylamine. In some embodiments, a medium contains methylamine, tributylamine, benzylamine, triethylamine, or a combination thereof, at a concentration of about 10 μM to about 3 mM, e.g., about 10 μM, about 50 μM, about 100 μM, about 150 μM, about 200 μM, about 250 μM, about 300 μM, about 350 μM, about 400 μM, about 450 μM, about 500 μM, about 550 μM, about 600 μM, about 650 μM, about 750 μM, about 800 μM, about 850 μM, about 900 μM, about 950 μM, about 1 mM, about 1.25 mM, about 1.5 mM, about 1.75 Mm, about 2 mM, about 2.25 mM, about 2.5 mM, about 2.75 mM, about 3 mM, or more.

In some embodiments, a polypeptide (e.g., antibody) preparation having targeted values of C-terminal variants is produced by culturing a cell expressing the polypeptide (e.g., antibody) in a medium having an elevated level glucose. In some embodiments, a medium contains glucose at a concentration of about 0.1 g/L to about 10 g/L, e.g., about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.1 g/L, about 1.2 g/L, about 1.3 g/L, about 1.4 g/L, about 1.5 g/L, about 1.6 g/L, about 1.7 g/L, about 1.8 g/L, about 1.9 g/L, about 2 g/L, about 2.1 g/L, about 2.2, g/L, about 2.3 g/L, about 2.4 g/L, about 2.5 g/L, about 2.6 g/L, about 2.7 g/L, about 2.8 g/L, about 2.9 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, or more.

In some embodiments, a polypeptide (e.g., antibody) preparation having targeted values of C-terminal variants is produced by culturing a cell expressing the polypeptide (e.g., antibody) in a medium having an elevated level of histidine, lysine, arginine, or a combination of histidine, lysine, and/or arginine. In some embodiments, a medium contains histidine, lysine, arginine, or a combination of histidine, lysine, and/or arginine, at a concentration of about 1 g/L to about 50 g/L, for example, at least about 1 g/L, at least about 1.5 g/L, at least about 2 g/L, at least about 2.5 g/L, at least about 3 g/L, at least about 3.5 g/L, at least about 4 g/L, at least about 4.5 g/L, at least about 5 g/L, at least about 5.5 g/L, at least about 6 g/L, at least about 6.5 g/L, at least about 7 g/L, at least about 7.5 g/L, at least about 8 g/L, at least about 8.5 g/L, at least about 9 g/L, at least about 9.5 g/L, at least about 10 g/L, at least about 10.5 g/L, at least about 11 g/L, at least about 11.5 g/L, at least about 12 g/L, at least about 12.5 g/L, at least about 13 g/L, at least about 13.5 g/L, at least about 14 g/L, at least about 14.5 g/L, at least about 15 g/L, at least about 15.5 g/L, at least about 16 g/L, at least about 16.5 g/L, at least about 17 g/L, at least about 17.5 g/L, at least about 18 g/L, at least about 18.5 g/L, at least about 19 g/L, at least about 19.5 g/L, at least about 20 g/L, at least about 25 g/L, at least about 30 g/L, at least about 35 g/L, at least about 40 g/L, at least about 45 g/L, at least about 50 g/L, or more.

In some embodiments, a polypeptide (e.g., antibody) preparation having targeted values of C-terminal variants is produced by culturing a cell expressing the polypeptide (e.g., antibody) in a medium having an elevated level of glutamine. In some embodiments, a medium contains glutamine at a concentration of about 5 mM to about 80 mM, e.g., about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, or more.

Cells can be cultured in a variety of cell culture media known in the art, which are modified according to the disclosure to include one or more carboxypeptidase activators, one or more carboxypeptidase inhibitors, and/or one or more pH modifying agents (e.g., at an elevated or reduced level) described herein. Cell culture medium is understood by those of skill in the art to refer to a nutrient solution in which cells, such as animal or mammalian cells, are grown. A cell culture medium generally includes one or more of the following components: an energy source (e.g., a carbohydrate such as glucose); amino acids; vitamins; lipids or free fatty acids; and trace elements, e.g., inorganic compounds or naturally occurring elements in the micromolar range. Cell culture medium can also contain additional components, such as hormones and other growth factors (e.g., insulin, transferrin, epidermal growth factor, serum, and the like); salts (e.g., calcium, magnesium and phosphate); buffers (e.g., HEPES); nucleosides and bases (e.g., adenosine, thymidine, hypoxanthine); antibiotics (e.g., gentamycin); and cell protective agents (e.g., a Pluronic polyol (Pluronic F68)).

Media that has been prepared or commercially available can be modified according to the present disclosure for utilization in the methods described herein. Nonlimiting examples of such media include Minimal Essential Medium (MEM, Sigma, St. Louis, Mo.); Ham's F10 Medium (Sigma); Dulbecco's Modified Eagles Medium (DMEM, Sigma); RPM I-1640 Medium (Sigma); HyClone cell culture medium (HyClone. Logan, Utah); Power CHO2 (Lonza Inc., Allendale, NJ); and chemically-defined (CD) media, which are formulated for particular cell types, e.g., CD-CHO Medium (Invitrogen. Carlsbad, Calif.). Culture medium suitable for the particular cells being cultured can be determined by a person of ordinary skill in the art without undue experimentation.

Cell culture conditions (including pH, $O_2$, $CO_2$, and temperature) suitable for cellular production of polypeptides described herein (e.g., antibodies) are those that are known in the art, such as conditions for batch, continuous, or fed-batch culturing of cells. For example, pH of cell culture medium is generally maintained at about 6.8 to about 7.6.

In general, cell culture methods are classified as batch culture, continuous culture, and fed-batch culture. Any of these culture methods can be used to grow cells that produce targeted levels of C-terminal variants.

In batch culture, a small amount of seed culture solution is added to a medium and cells are grown without any addition of a new medium or discharge of the culture solution during the culture. For the production of targeted levels of C-terminal variants using batch culture, the medium comprises an elevated level or a reduced level of one or more carboxypeptidase activator(s), one or more carboxypeptidase inhibitor(s), and/or one or more a pH1 modifying agents from an initial stage of the cell culture.

In some embodiments, a polypeptide (e.g., antibody) preparation having targeted values of C-terminal variants is produced by batch culture of cells expressing the polypeptide in a medium having at least about 2 g/L arginine, at least about 2 g/L lysine, at least about 2 g/L of histidine, at least about 2 g/L of a combination of arginine, lysine and/or histidine, at least about 5 mM $NH_4Cl$, about 10 μM to about 500 μM chloroquine, about 10 mM to about 30 mM glutamine, and/or about 0.5 g/L to about 2 g/L glucose.

Continuous culture is a culture method in which a medium is added and discharged continuously during the culture. This continuous method includes perfusion culture. For example, in the production of targeted levels of C-terminal variants using continuous culture, the medium added during the culture can have an elevated level or a reduced level of one or more carboxypeptidase activator(s), one or more carboxypeptidase inhibitor(s), and/or one or more pH modifying agents. In certain methods, the initial culture medium does not include an elevated level or a reduced level of one or more carboxypeptidase activator(s), one or more carboxypeptidase inhibitor(s), and/or one or more pH modifying agents, but at a particular time point during the continuous culture (such as during production phase), the medium added during the culture is elevated or reduced in the level of one or more carboxypeptidase activator(s), one or more carboxypeptidase inhibitor(s), and/or one or more pH1 modifying agents.

In some embodiments, a polypeptide (e.g., antibody) preparation having targeted values of C-terminal variants is produced by continuous culture of cells expressing the polypeptide in a medium having at least about 2 g/L arginine, at least about 2 g/L lysine, at least about 2 g/L of histidine, at least about 2 g/L of a combination of arginine, lysine and/or histidine, at least about 5 mM $NH_4Cl$, about 10 μM to about 500 μM chloroquine, about 10 mM to about 30 mM glutamine, and/or about 0.5 g/L to about 2 g/L glucose.

Fed-batch culture is a method between batch culture and continuous culture. In a fed-batch culture, a medium is fed continuously or sequentially during the culture, but unlike the continuous culture, discharge of the culture solution is not carried out during the culture. For example, for the production of targeted levels of C-terminal variants using fed-batch culture, the medium added during the culture can have an elevated level or a reduced level of one or more carboxypeptidase activators, one or more carboxypeptidase inhibitors, and/or one or more pH modifying agents.

In some embodiments, a polypeptide (e.g., antibody) preparation having targeted values of C-terminal variants is produced by adding medium to a fed batch culture of cells expressing the polypeptide sufficient to achieve at least about 2 g/L arginine, at least about 2 g/L lysine, at least about 2 g/L of histidine, at least about 2 g/L of a combination of arginine, lysine and/or histidine, at least about 5 mM $NH_4Cl$, about 10 µM to about 500 µM chloroquine, about 10 mM to about 30 mM glutamine, and/or about 0.5 g/L to about 2 g/L glucose, in the culture medium.

According to the present disclosure, cell culture can be carried out under conditions for the large or small scale production of polypeptides (e.g., antibodies), using culture vessels and/or culture apparatuses that are conventionally employed for animal or mammalian cell culture. For example, tissue culture dishes, T-flasks, shaker flasks, and spinner flasks can be used on a laboratory scale. For culturing on a larger scale (e.g., 500 L, 5000 L, or more), a fluidized bed bioreactor, a hollow fiber bioreactor, a roller bottle culture, or a stirred tank bioreactor system can be used (e.g., as described in U.S. Pat. Nos. 7,541,164 and 7,332,303).

In particular methods, the level of C-terminal variants in a preparation of polypeptides (e.g., antibodies) is monitored during a particular cell culture, thereby allowing adjustment (e.g., increasing or decreasing the amount of one or more carboxypeptidase inhibitors, one or more carboxypeptidase activators, and/or one or more pH modifying agents in the culture) or possibly termination of the culture in order, for example, to achieve a target level of C-terminal variants.

Polypeptides

The methods described herein can be used to produce any polypeptide of interest, such as an antibody, an Fc-containing polypeptide, and/or a fusion protein.

The basic structure of an IgG antibody consists of two identical light polypeptide chains and two identical heavy polypeptide chains linked together by disulfide bonds. The first domain located at the amino terminus of each chain is variable in amino acid sequence, providing the antibody binding specificities found in each individual antibody. These are known as variable heavy (VH) and variable light (VL) regions. The other domains of each chain are relatively invariant in amino acid sequence and are known as constant heavy (CH) and constant light (CL) regions. For an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

The nucleic acid sequences encoding antibodies and Fc-containing polypeptides typically encode a lysine residue at the C-terminus of the heavy chains. C-terminal lysines, however, are often absent, or are present at reduced levels, in antibodies and Fc-containing polypeptides isolated from mammalian cell cultures. In some embodiments, the present methods can increase the amount of lysine residues on antibodies or Fc-containing polypeptides in an antibody preparation or a preparation of Fc-containing polypeptides. As used herein, "K0" means an antibody or Fc-containing polypeptide not having a lysine residue on either heavy chain C-terminus. As used herein, "K1" means an antibody or Fc-containing polypeptide having a lysine residue on one heavy chain C-terminus. As used herein, "K2" means an antibody or Fc-containing polypeptide having a lysine residue on each heavy chain C-terminus.

Antibodies can include, for example, monoclonal antibodies, polyclonal antibodies, multispecific antibodies, human antibodies, humanized antibodies, camelized antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA and IgY), class (e.g., IgG1, IgG2, IgG3, IgG4, IgA1 and IgA2) or subclass.

The term "Fc fragment", as used herein, refers to one or more fragments of an Fc region that retains an Fc function and/or activity, such as binding to an Fc receptor. Examples of such fragments include fragments that include an N-linked glycosylation site of an Fe region (e.g., an Asn297 of an IgG heavy chain or homologous sites of other antibody isotypes), such as a CH2 domain. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a $F(ab')_2$ fragment, a Fd fragment, a Fv fragment, a scFv fragment, a dAb fragment (Ward et al., (1989) *Nature* 341:544-546), and an isolated complementarity determining region (CDR). These antibody fragments can be obtained using conventional techniques known to those with skill in the art, and the fragments can be screened for utility in the same manner as are intact antibodies.

Antibodies or fragments of the compositions and methods described herein can be produced by any method known in the art for the synthesis of antibodies (see, e.g., Harlow et al., *Antibodies: A Laboratory Manual*, (Cold Spring Harbor Laboratory Press, 2nd ed. 1988); Brinkman et al., 1995, *J. Immunol. Methods* 182:41-50; WO 92/22324; WO 98/46645). Chimeric antibodies can be produced using the methods described in, e.g., Morrison, 1985, *Science* 229: 1202, and humanized antibodies by methods described in, e.g., U.S. Pat. No. 6,180,370.

Additional antibodies of the compositions and methods described herein are bispecific antibodies and multivalent antibodies, as described in, e.g., Segal et al., *J. Immunol. Meth.* 248:1-6 (2001); and Tutt et al., *J. Immunol.* 147: 60 (1991).

Fc-containing polypeptides include, without limitation, fusion proteins, e.g., Fc regions or Fc fragments conjugated or fused to one or more heterologous moieties. Heterologous moieties include, but are not limited to, peptides, polypeptides, proteins, fusion proteins, nucleic acid molecules, small molecules, mimetic agents, synthetic drugs, inorganic molecules, and organic molecules. In some instances, an Fc-containing polypeptide is or includes a fusion protein comprising a peptide, polypeptide, protein scaffold, scFv, dsFv, diabody, Tandab, or an antibody mimetic fused to an Fc region, such as a glycosylated Fc region. The fusion protein can include a linker region connecting the Fc region to the heterologous moiety (see, e.g., Hallewell et al. (1989), *J. Biol. Chem.* 264, 5260-5268; Alfthan et al. (1995) *Protein Eng.* 8:725-731).

In some instances, an Fc-containing polypeptide is or includes an Fc region conjugated to a heterologous polypeptide of at least 10, at least 20, at least 30, at least 40, at least 50, at least 60, at least 70, at least 80, at least 90 or at least 100 amino acids. In some instances, an Fc-containing polypeptide is or includes an Fc region (or an Fc fragment) conjugated to a marker sequence, such as a peptide to facilitate purification. A particular marker amino acid sequence is a hexa-histidine peptide, such as the tag provided in a pQE vector (QIAGEN, Inc., 9259 Eton Avenue, Chatsworth, Calif., 91311). Other peptide tags useful for purification include, but are not limited to, the hemagglutinin "HA" tag, which corresponds to an epitope derived from the influenza hemagglutinin protein (Wilson et al., 1984, *Cell* 37:767) and the "Flag" tag.

In other instances, an Fc-containing polypeptide is or includes an Fc region conjugated to a diagnostic or detectable agent. Such Fc-containing polypeptides can be useful for monitoring or prognosing the development or progression of disease or disorder as part of a clinical testing procedure, such as determining the efficacy of a particular therapy. Such diagnosis and detection can be accomplished by coupling the glycoprotein to detectable substances including, but not limited to, various enzymes, such as but not limited to horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and acquorin; radioactive materials, such as but not limited to iodine ($^{131}$I, $^{125}$I, $^{123}$I), carbon ($^{14}$C), sulfur ($^{35}$S), tritium ($^{3}$H), indium ($^{115}$In, $^{113}$In, $^{112}$I, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{153}$Gd, $^{159}$Gd, $^{149}$Pm, $^{140}$La, $^{169}$Yb, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{51}$Cr, $^{54}$Mn, $^{75}$Se, $^{113}$Sn. and $^{117}$Sn; positron emitting metals using various positron emission tomographies, non-radioactive paramagnetic metal ions, and molecules that are radiolabelled or conjugated to specific radioisotopes.

Techniques for conjugating therapeutic moieties to antibodies and/or Fc-containing polypeptides are well known (see, e.g., Arnon et al., "Monoclonal Antibodies For Immunotargeting Of Drugs In Cancer Therapy", in *Monoclonal Antibodies and Cancer Therapy*, Reisfeld et al. (eds.), pp. 243-56. (Alan R. Liss, Inc. 1985); Hellstrom et al., "Antibodies For Drug Delivery", in *Controlled Drug Delivery* (2nd Ed.). Robinson et al. (eds.), pp. 623-53 (Marcel Dekker, Inc. 1987)).

Nonlimiting, exemplary polypeptides that can be produced using the methods described herein include abatacept (Orencia®, Bristol-Myers Squibb), abciximab (ReoPro®, Roche), adalimumab (Humira®, Bristol-Myers Squibb), alefacept (Amevive®, Astellas Pharma), alemtuzumab (Campath®, Genzyme/Bayer), basiliximab (Simulect®, Novartis), bevacizumab (Avastin®, Roche), certolizumab (CIMZIA®, UCB, Brussels, Belgium), cetuximab (Erbitux®, Merck-Serono), daclizumab (Zenapax®, Hoffmann-La Roche), denileukin diftitox (Ontak®, Eisai), eculizumab (Soliris®, Alexion Pharmaceuticals), efalizumab (Raptiva®, Genentech), etanercept (Enbrel®, Amgen-Pfizer), gemtuzumab (Mylotarg®, Pfizer), ibritumomab (Zevalin®, Spectrum Pharmaceuticals), infliximab (Remicade®, Centocor), muromonab (Orthoclone OKT3®, Janssen-Cilag), natalizumab (Tysabri®, Biogen Idec, Elan), omalizumab (Xolair®, Novartis), palivizumab (Synagis®, MedImmune), panitumumab (Vectibix®, Amgen), ranibizumab (Lucentis®, Genentech), rilonacept (Arcalyst®, Regeneron Pharmaceuticals), rituximab (MabThera®, Roche), tositumomab (Bexxar®, GlaxoSmithKline), and trastuzumab (Herceptin®, Roche).

A recombinant polypeptide described herein (e.g., an antibody) can be incorporated into a pharmaceutical composition. Such a pharmaceutical composition is useful in the prevention and/or treatment of diseases. Pharmaceutical compositions comprising a polypeptide (e.g., an antibody) can be formulated by methods known to those skilled in the art. The pharmaceutical composition can be administered parenterally in the form of an injectable formulation comprising a sterile solution or suspension in water or another pharmaceutically acceptable liquid. For example, the pharmaceutical composition can be formulated by suitably combining the polypeptide with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

A suitable means of administration can be selected based on the age and condition of the patient. A single dose of the pharmaceutical composition containing a polypeptide (e.g., antibody) can be selected from a range of 0.001 mg/kg of body weight to 1000 mg/kg of body weight. On the other hand, a dose can be selected in the range of 0.001 mg/kg of body weight to 100000 mg/kg of body weight, but the present disclosure is not limited to such ranges. The dose and method of administration varies depending on the weight, age, condition, and the like of the patient, and can be suitably selected as needed by those skilled in the art.

In other instances, a recombinant polypeptide (e.g., antibody) can be used to screen for disease or for agents that can treat or prevent disease.

Methods of Assaying Levels of C-Terminal Variants and Polypeptide Activity

The level of C-terminal variants of a reference polypeptide (e.g., a reference antibody) can be assayed by known methods (see, e.g., Dick et al., *Biotechnol. Bioeng.* 100: 1132-1143 (2008)). For example, polypeptides (e.g., antibodies) can be analyzed by chromatographic methods, including but not limited to, liquid chromatography (LC), high performance liquid chromatography (HPLC), ultra performance liquid chromatography (UPLC), thin layer chromatography (TLC), amide column chromatography, and combinations thereof.

In other methods, polypeptides (e.g., antibodies) are analyzed by mass spectrometry (MS) and related methods, including but not limited to, tandem MS, LC-MS. LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof.

Other methods of analyzing polypeptides (e.g., antibodies) include electrophoretic methods, including but not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific amino acids, and combinations thereof.

Yet other analysis methods include nuclear magnetic resonance (NMR) and related methods, including but not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some instances, the level of C-terminal variants in a preparation of polypeptides (e.g., level of g K0, K1, and/or K2 lysine variants in a preparation of antibodies or Fc-containing polypeptides), produced using a method described herein can be compared to a target value (e.g., reference standard), e.g., to make a decision regarding the composition of the polypeptide preparation, e.g., a decision to classify, select, accept or discard, release or withhold, process into a drug product, ship, move to a different location, formulate, label, package, release into commerce, or sell or offer for sale the polypeptide, e.g., a recombinant antibody. In other instances, the decision can be to accept, modify or reject a production parameter or parameters used to make the polypeptide, e.g., an antibody. Particular, non-limiting examples of reference standards include a control level (e.g., a polypeptide produced by a different method) or a range or value in a product specification (e.g., an FDA label or Physician's Insert) or quality criterion for a pharmaceutical preparation containing the polypeptide preparation.

In some instances, methods (i.e., evaluation, identification, and production methods) include taking action (e.g., physical action) in response to the methods disclosed herein. For example, a polypeptide preparation is classified, selected, accepted or discarded, released or withheld, processed into a drug product, shipped, moved to a different location, formulated, labeled, packaged, released into commerce, or sold or offered for sale, depending on whether the preselected or target value is met. In some instances, processing may include formulating (e.g., combining with pharmaceutical excipients), packaging (e.g., in a syringe or vial), labeling, or shipping at least a portion of the polypeptide preparation. In some instances, processing includes formulating (e.g., combining with pharmaceutical excipients), packaging (e.g., in a syringe or vial), and labeling at least a portion of the preparation as a drug product described herein. Processing can include directing and/or contracting another party to process as described herein.

In some instances, a biological activity of a polypeptide preparation (e.g., an antibody preparation) is assessed. Biological activity of the preparation can be analyzed by any known method. In some embodiments, a binding activity of a polypeptide is assessed (e.g., binding to a receptor). In some embodiments, a therapeutic activity of a polypeptide is assessed (e.g., an activity of a polypeptide in decreasing severity or symptom of a disease or condition, or in delaying appearance of a symptom of a disease or condition). In some embodiments, a pharmacologic activity of a polypeptide is assessed (e.g., bioavailability, pharmacokinetics, pharmacodynamics). For methods of analyzing bioavailability, pharmacokinetics, and pharmacodynamics of glycoprotein therapeutics, see, e.g., Weiner et al., *J. Pharm. Biomed. Anal.* 15(5):571-9, 1997; Srinivas et al., *J. Pharm. Sci.* 85(1):1-4, 1996; and Srinivas et al., *Pharm. Res.* 14(7):911-6, 1997.

The particular biological activity or therapeutic activity that can be tested will vary depending on the particular polypeptide (e.g., antibody). The potential adverse activity or toxicity (e.g., propensity to cause hypertension, allergic reactions, thrombotic events, seizures, or other adverse events) of polypeptide preparations can be analyzed by any available method. In some embodiments, immunogenicity of a polypeptide preparation is assessed, e.g., by determining whether the preparation elicits an antibody response in a subject.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following example. The example is provided for illustrative purposes only. It is not to be construed as limiting the scope or content of the disclosure in any way.

EXAMPLE

Preparation of Antibody with Increased K1 and K2 Lysine Residues

Method

The carboxyl-terminal lysine residues of a model antibody produced by CHO cells were analyzed. CL320 CHO cells were grown in a shake flask initially in base media (Power CHO2, Catalog #BE15-771, Lonza Inc., Allendale, NJ) with 4 mM L-Gln and no other supplements. Cells were grown for 4 days, and the number of cells increased from 0.54E6/mL to 4E6/mL. On Day 4, the cells were fed with 20% Lonza Power Feed A medium or with 20% Power Feed A medium supplemented with 10 g/L L-Lys or L-Arg. On Day 5, 10 g/L cottonseed hydrolysate was added. VCD and viability were assessed, and cells were harvested on Day 10. The antibodies produced under the various conditions were evaluated for titer and C-terminal lysine by ion exchange chromatography.

Results

As shown in FIG. 1, antibodies from cells fed with L-Lys Feed or with L-Arg Feed both had levels of K1 and K2 lysine similar to that of a sample of Humira®. Surprisingly, addition of 10 mg/L L-Lys or 10 mg/L L-Arg did not affect growth, viability, or titers. Addition of a combination of L-Lys (10 mg/L) and L-Arg (10 mg/L) resulted in cell death, which may have been the result of not adjusting the pH to appropriate cell culture levels.

Further, when the antibodies produced were subsequently digested with carboxypeptidase, the levels of K1 and K2 lysine residues returned to baseline, indicating that the levels of K1 and K2 were not due to nonspecific charge differences (e.g., due to amidation of the antibody).

Additional data showed that a controlled glucose feed resulted in increased levels of K1 lysines compared to bolus glucose feeds. Without wishing to be bound by theory, it is believed that by controlling glucose levels during culture, lactate levels can be reduced, resulting in increased intracellular pH.

Further data showed that the inclusion of $NH_4Cl$ in culture media resulted in increased levels of K1 and K2 lysine residues compared to controls.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A preparation of recombinant antibody having a target level of C-terminal variants, wherein the C-terminal variants comprise one or more of a K1 lysine variant of the recombinant antibody and a K2 lysine variant of the recombinant antibody,
wherein the K1 lysine variant has a lysine residue at one heavy chain C-terminus,
wherein the K2 lysine variant has a lysine residue at each heavy chain C-terminus,
wherein the target level of C-terminal variants comprises (i) 12% to 25% K1 lysine variants, relative to total recombinant antibody in the preparation or (ii) 2% to 10% K2 lysine variants, relative to total recombinant antibody in the preparation or both (i) and (ii), and
wherein the preparation of recombinant antibody is produced by expressing the recombinant antibody in a cell cultured in a medium comprising 2 g/L lysine to 20 g/L lysine.

2. The preparation of claim 1, wherein the medium comprises 3 g/L lysine to 10 g/L lysine.

3. The preparation of claim 1, wherein the medium comprises 5 g/L lysine to 10 g/L lysine.

4. The preparation of claim 1, wherein the medium comprises 5 g/L lysine.

5. The preparation of claim 1, wherein the target level of C-terminal variants comprises (i) 12% to 25% K1 lysine variants, relative to total recombinant antibody in the preparation and (ii) 2% to 10% K2 lysine variants, relative to total recombinant antibody in the preparation.

6. The preparation of claim 1, wherein the target level comprises 15% to 20% of K1 lysine variants, relative to total recombinant antibody in the preparation.

7. The preparation of claim 1, wherein the target level comprises 3% to 5% K2 lysine variants, relative to total recombinant antibody in the preparation.

8. The preparation of claim 1, wherein the target level of C-terminal variants comprises (i) 15% to 20% K1 lysine variant, relative to total recombinant antibody in the preparation and (ii) 3% to 5% K2 lysine variants, relative to total recombinant antibody in the preparation.

9. The preparation of claim 1, wherein the target level of C-terminal variants is increased relative to a preparation of the recombinant antibody produced using a medium not comprising 2 g/L lysine to 20 g/L lysine.

10. The preparation of claim 1, wherein the recombinant antibody is adalimumab.

11. The preparation of claim 5, wherein the recombinant antibody is adalimumab.

12. The preparation of claim 8, wherein the recombinant antibody is adalimumab.

13. The preparation of claim 1, wherein the cell is a mammalian cell.

14. The preparation of claim 1, wherein the cell is a CHO cell.

15. The preparation of claim 1, wherein the medium has a pH of 6.8 to 7.0.

16. The preparation of claim 1, wherein the medium has a pH of 6.9.

17. The preparation of claim 1, wherein the cell is cultured at a temperature of 34° C. to 37° C.

18. The preparation of claim 1, wherein the cell is cultured at a temperature of 36° C.

19. A preparation of recombinant antibody having a target level of C-terminal variants, wherein the C-terminal variants comprise a K1 lysine variant of the recombinant antibody and a K2 lysine variant of the recombinant antibody,
wherein the K1 lysine variant has a lysine residue at one heavy chain C-terminus,
wherein the K2 lysine variant has a lysine residue at each heavy chain C-terminus,
wherein the target level of C-terminal variants comprises (i) 12% to 25% K1 lysine variants, relative to total recombinant antibody in the preparation, and (ii) 2% to 10% K2 lysine variants, relative to total recombinant antibody in the preparation, and
wherein the preparation of recombinant antibody is produced by expressing the recombinant antibody in a CHO cell cultured in a medium comprising 2 g/L lysine to 20 g/L lysine, said medium having a pH of 6.8 to 7.0.

20. The preparation of claim 18, wherein the recombinant antibody is adalimumab.

* * * * *